United States Patent
Kahn

(10) Patent No.: US 12,224,059 B2
(45) Date of Patent: *Feb. 11, 2025

(54) SYSTEMS AND METHODS FOR NETWORK-BASED COUNSELING

(71) Applicant: TELADOC HEALTH, INC., Purchase, NY (US)

(72) Inventor: Justin Kahn, Salt Lake City, UT (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/971,796

(22) Filed: Oct. 24, 2022

(65) Prior Publication Data

US 2023/0253107 A1 Aug. 10, 2023

Related U.S. Application Data

(63) Continuation of application No. 14/982,914, filed on Dec. 29, 2015, now Pat. No. 11,482,326, which is a
(Continued)

(51) Int. Cl.
*G16H 80/00* (2018.01)
*G06Q 10/0631* (2023.01)
*G06Q 40/08* (2012.01)
*G16H 40/63* (2018.01)
*G16H 40/67* (2018.01)
(Continued)

(52) U.S. Cl.
CPC ..... *G16H 40/67* (2018.01); *G06Q 10/063112* (2013.01); *G06Q 40/08* (2013.01); *G16H 40/63* (2018.01); *G16H 80/00* (2018.01); *H04L 65/1059* (2013.01); *H04L 65/1069* (2013.01);
(Continued)

(58) Field of Classification Search
CPC ................ G16H 80/00; G06F 19/3418; G06Q 50/22–24
See application file for complete search history.

(56) References Cited

U.S. PATENT DOCUMENTS 3,821,995 A 7/1974 Aghnides
4,107,689 A 8/1978 Jellinek
(Continued)

FOREIGN PATENT DOCUMENTS

AU 1216200 A 5/2000
CA 2289697 A1 11/1998
(Continued)

OTHER PUBLICATIONS

Appeal from the U.S. District Court for the Central District of California in case No. 11-cv-9185, Judge Percy Anderson, Joint Appendix, vol. I of IV, Jun. 24, 2013, pp. A1-A6357.
(Continued)

*Primary Examiner* — John A Pauls

(57) ABSTRACT

Aspects of the present invention relate to facilitating remote expert consultation using a web site that provides for video conferencing between clients and experts who are have been vetted through registration in the system. Some aspects relate to transmission of correlated physiological characteristic data simultaneously with a video conference. Some aspects relate to control of conferencing functions through client and expert web pages.

7 Claims, 7 Drawing Sheets

Related U.S. Application Data continuation-in-part of application No. 13/372,365, filed on Feb. 13, 2012, now Pat. No. 8,718,245.

(60) Provisional application No. 61/545,992, filed on Oct. 11, 2011, provisional application No. 61/443,657, filed on Feb. 16, 2011.

(51) Int. Cl.

| | | |
|---|---|---|
| *H04L 65/1059* | (2022.01) | |
| *H04L 65/1069* | (2022.01) | |
| *H04L 65/402* | (2022.01) | |
| *H04L 65/403* | (2022.01) | |
| *H04L 67/12* | (2022.01) | |

(52) U.S. Cl.
CPC ...... *H04L 65/4025* (2022.05); *H04L 65/4046* (2013.01); *H04L 67/12* (2013.01)

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George, II et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-malek |
| 5,517,251 A | 5/1996 | Rector et al. |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,531 A | 11/1997 | Li et al. |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,799,055 A | 8/1998 | Peshkin et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | Devault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |

(56) References Cited

U.S. PATENT DOCUMENTS

| | | |
|---|---|---|
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,313,853 B1 | 11/2001 | Lamontagne et al. |
| 6,314,631 B1 | 11/2001 | Pryor |
| 6,317,652 B1 | 11/2001 | Osada |
| 6,317,776 B1 | 11/2001 | Broussard et al. |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,331,181 B1 | 12/2001 | Tierney et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Nada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | Mcelvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury, Jr. et al. |
| 6,691,000 B2 | 2/2004 | Nagai et al. |
| 6,693,585 B1 | 2/2004 | Macleod |
| 6,710,797 B1 | 3/2004 | Mcnelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,763,284 B2 | 7/2004 | Watanabe et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |

(56) References Cited

U.S. PATENT DOCUMENTS

| | | |
|---|---|---|
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | Mclurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | Mccall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,797,168 B2 | 9/2010 | Kusumoto et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 7,995,652 B2 | 8/2011 | Washington |
| 7,996,264 B2 | 8/2011 | Kusumoto et al. |
| 8,072,481 B1 | 12/2011 | Mcnelley et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,384,755 B2 | 2/2013 | Wang et al. |
| 8,400,491 B1 | 3/2013 | Panpaliya et al. |
| 8,401,275 B2 | 3/2013 | Wang et al. |
| 8,423,284 B2 | 4/2013 | O'shea |
| 8,451,731 B1 | 5/2013 | Lee et al. |
| 8,463,435 B2 | 6/2013 | Herzog et al. |
| 8,489,641 B1 | 7/2013 | Seefeld et al. |
| 8,503,340 B1 | 8/2013 | Xu |
| 8,515,577 B2 | 8/2013 | Wang et al. |
| 8,527,094 B2 | 9/2013 | Kumar et al. |
| 8,531,502 B2 | 9/2013 | Cheng et al. |
| 8,532,860 B2 | 9/2013 | Daly |
| 8,588,976 B2 | 11/2013 | Mangaser et al. |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,718,245 B2 | 5/2014 | Kahn |
| 8,726,454 B2 | 5/2014 | Gilbert et al. |
| 8,750,906 B2 | 6/2014 | Winkler et al. |
| 8,776,043 B1 | 7/2014 | Thimsen et al. |
| 8,780,165 B2 | 7/2014 | Wang et al. |

(56) References Cited

U.S. PATENT DOCUMENTS

| | | |
|---|---|---|
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 8,983,174 B2 | 3/2015 | Wang et al. |
| 9,098,611 B2 | 8/2015 | Pinter et al. |
| 9,147,284 B2 | 9/2015 | Keene et al. |
| 9,374,394 B2 | 6/2016 | Kahn |
| 11,482,326 B2 | 10/2022 | Kahn |
| 2001/0002448 A1 | 5/2001 | Wilson et al. |
| 2001/0010053 A1 | 7/2001 | Ben-shachar et al. |
| 2001/0010541 A1 | 8/2001 | Fernandez et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0010596 A1 | 1/2002 | Matory et al. |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0029350 A1 | 3/2002 | Cooper et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Athan et al. |
| 2002/0123941 A1 | 9/2002 | Donahue et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183598 A1 | 12/2002 | Teraura et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2002/0193908 A1 | 12/2002 | Parker et al. |
| 2003/0021107 A1 | 1/2003 | Howell et al. |
| 2003/0028399 A1* | 2/2003 | Davis .................. G16Z 99/00 705/2 |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0069828 A1 | 4/2003 | Blazey et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1 | 11/2003 | Mckee |
| 2003/0216833 A1 | 11/2003 | Mukai et al. |
| 2003/0216834 A1 | 11/2003 | Allard |
| 2003/0220541 A1 | 11/2003 | Salisbury, Jr. et al. |
| 2003/0220715 A1 | 11/2003 | Kneifel, II et al. |
| 2003/0231244 A1 | 12/2003 | Bonilla et al. |
| 2003/0232649 A1 | 12/2003 | Gizis et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | Mclurkin et al. |
| 2004/0041904 A1 | 3/2004 | Lapalme et al. |
| 2004/0048633 A1 | 3/2004 | Sato et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0078436 A1 | 4/2004 | Demsky et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0140404 A1 | 7/2004 | Ohta et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0202281 A1 | 10/2004 | Colbeth et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0233894 A1 | 11/2004 | Rutland |

(56) References Cited

U.S. PATENT DOCUMENTS

| | | |
|---|---|---|
| 2004/0240981 A1 | 12/2004 | Dothan et al. |
| 2004/0241981 A1 | 12/2004 | Doris et al. |
| 2004/0243712 A1 | 12/2004 | Sakai et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0075544 A1 | 4/2005 | Shapiro et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | Mcgee et al. |
| 2005/0264648 A1 | 12/2005 | Ivashin et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0119701 A1 | 6/2006 | King |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0238379 A1 | 10/2006 | Kimchi et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0016328 A1 | 1/2007 | Ziegler et al. |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0061041 A1 | 3/2007 | Zweig |
| 2007/0064092 A1 | 3/2007 | Sandbeg et al. |
| 2007/0067734 A1 | 3/2007 | Cunningham et al. |
| 2007/0078566 A1 | 4/2007 | Wang et al. |
| 2007/0093279 A1 | 4/2007 | Janik |
| 2007/0112700 A1 | 5/2007 | Den Haan et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0182811 A1 | 8/2007 | Rockefeller et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0002022 A1 | 1/2008 | Vanepps |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |

(56) References Cited

U.S. PATENT DOCUMENTS

| | | |
|---|---|---|
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0259155 A1 | 10/2008 | Mclelland et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0285886 A1 | 11/2008 | Allen et al. |
| 2008/0306375 A1 | 12/2008 | Sayler et al. |
| 2009/0021572 A1 | 1/2009 | Garudadri et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0173846 A1 | 7/2009 | Katz |
| 2009/0177323 A1 | 7/2009 | Ziegler et al. |
| 2009/0177641 A1 | 7/2009 | Raghavan |
| 2009/0220075 A1 | 9/2009 | Sidhu et al. |
| 2009/0234499 A1 | 9/2009 | Nielsen et al. |
| 2009/0237317 A1 | 9/2009 | Rofougaran |
| 2009/0240371 A1 | 9/2009 | Wang et al. |
| 2009/0248041 A1 | 10/2009 | Williams et al. |
| 2009/0248200 A1 | 10/2009 | Root |
| 2009/0259339 A1 | 10/2009 | Wright et al. |
| 2009/0326979 A1 | 12/2009 | Ryan |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0199089 A1 | 8/2010 | Vysogorets et al. |
| 2010/0228249 A1 | 9/2010 | Mohr et al. |
| 2010/0268383 A1 | 10/2010 | Wang et al. |
| 2010/0274579 A1 | 10/2010 | Marten et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0118748 A1 | 5/2011 | Itkowitz |
| 2011/0153198 A1 | 6/2011 | Kokkas et al. |
| 2011/0169832 A1 | 7/2011 | Brown et al. |
| 2011/0172822 A1 | 7/2011 | Ziegler et al. |
| 2011/0187875 A1 | 8/2011 | Sanchez et al. |
| 2011/0190665 A1 | 8/2011 | Bedingham et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0224998 A1 | 9/2011 | Schoenberg |
| 2011/0224999 A1 | 9/2011 | Baccarella-garcia |
| 2011/0245973 A1 | 10/2011 | Wang et al. |
| 2011/0249079 A1 | 10/2011 | Santamaria et al. |
| 2011/0280551 A1 | 11/2011 | Sammon |
| 2011/0288417 A1 | 11/2011 | Pinter et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0040646 A1 | 2/2012 | Garg et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0092438 A1 | 4/2012 | Guzman et al. |
| 2012/0095352 A1 | 4/2012 | Tran |
| 2012/0113856 A1 | 5/2012 | Krishnaswamy |
| 2012/0179479 A1* | 7/2012 | Waterson ............... G16H 80/00 705/2 |
| 2012/0182392 A1 | 7/2012 | Kearns et al. |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0215380 A1 | 8/2012 | Fouillade et al. |
| 2012/0218374 A1 | 8/2012 | Matula et al. |
| 2012/0220372 A1 | 8/2012 | Cheung et al. |
| 2012/0242279 A1 | 9/2012 | Tso et al. |
| 2012/0291809 A1 | 11/2012 | Kuhe et al. |
| 2012/0320145 A1 | 12/2012 | Kahn |
| 2013/0035138 A1 | 2/2013 | Abbott |
| 2013/0158720 A1 | 6/2013 | Zywicki et al. |
| 2013/0250938 A1 | 9/2013 | Anandakumar et al. |
| 2013/0317842 A1 | 11/2013 | Schoenberg |
| 2013/0321257 A1 | 12/2013 | Moore et al. |
| 2014/0015914 A1 | 1/2014 | Delaunay |
| 2014/0032244 A1 | 1/2014 | Kolls et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0229547 A1 | 8/2014 | Justin |
| 2014/0250191 A1 | 9/2014 | Altman et al. |
| 2015/0119652 A1 | 4/2015 | Hyde et al. |
| 2016/0048841 A1 | 2/2016 | Johnson et al. |
| 2016/0094611 A1 | 3/2016 | Chow et al. |
| 2016/0219435 A1* | 7/2016 | Mistry ............... H04L 65/403 |
| 2016/0246936 A1 | 8/2016 | Kahn |
| 2019/0147141 A9 | 5/2019 | Kahn |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |

(56) References Cited

FOREIGN PATENT DOCUMENTS

| | | |
|---|---|---|
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 0466492 A2 | 1/1992 |
| EP | 0488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| EP | 2300930 B1 | 7/2015 |
| GB | 2431261 A | 4/2007 |
| JP | H07-194609 A | 8/1995 |
| JP | H07-213753 A | 8/1995 |
| JP | H07-248823 A | 9/1995 |
| JP | H07-257422 A | 10/1995 |
| JP | H08-84328 A | 3/1996 |
| JP | H08-320727 A | 12/1996 |
| JP | H09-267276 A | 10/1997 |
| JP | H10-79097 A | 3/1998 |
| JP | H10-288689 A | 10/1998 |
| JP | H11-220706 A | 8/1999 |
| JP | 2000-032319 A | 1/2000 |
| JP | 2000-049800 A | 2/2000 |
| JP | 2000-079587 A | 3/2000 |
| JP | 2000-196876 A | 7/2000 |
| JP | 2001-125641 A | 5/2001 |
| JP | 2001-147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2002-000574 A | 1/2002 |
| JP | 2002-046088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 T | 8/2004 |
| JP | 2004-261941 A | 9/2004 |
| JP | 2004-289379 A | 10/2004 |
| JP | 2005-028066 A | 2/2005 |
| JP | 2005-059170 A | 3/2005 |
| JP | 2005-111083 A | 4/2005 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-007040 A | 1/2007 |
| JP | 2007-081646 A | 3/2007 |
| JP | 2007-232208 A | 9/2007 |
| JP | 2007-316966 A | 12/2007 |
| JP | 2009-125133 A | 6/2009 |
| JP | 2010-064154 A | 3/2010 |
| JP | 2010-532109 A | 9/2010 |
| JP | 2010-246954 A | 11/2010 |
| KR | 10-2006-0037979 A | 5/2006 |
| KR | 10-2009-0012542 A | 2/2009 |
| KR | 10-2010-0019479 A | 2/2010 |
| KR | 10-2010-0139037 A | 12/2010 |
| WO | 1993/06690 A1 | 4/1993 |
| WO | 1997/42761 A1 | 11/1997 |
| WO | 1998/51078 A1 | 11/1998 |
| WO | 1999/67067 A1 | 12/1999 |
| WO | 2000/025516 A1 | 5/2000 |
| WO | 2000/033726 A1 | 6/2000 |
| WO | 2001/31861 A1 | 5/2001 |
| WO | 2003/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007/041295 A2 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |
| WO | 2013/097264 A1 | 7/2013 |

OTHER PUBLICATIONS

Appeal from the U.S. District Court for the Central District of California in case No. 11-cv-9185, Judge Percy Anderson, Joint Appendix, vol. II of IV, Jun. 24, 2013, pp. A6849-A10634.

Appeal from the U.S. District Court for the Central District of California in case No. 11-cv-9185, Judge Percy Anderson, Joint Appendix, vol. III of IV, Jun. 24, 2013, pp. A10654-A15517.

Appeal from the U.S. District Court for the Central District of California in case No. 11-cv-9185, Judge Percy Anderson, Joint Appendix, vol. IV of IV, Jun. 24, 2013, pp. A15677-A18127.

Appeal from the U.S. District Court for the Central District of California in No. 11-CV-9185, Judge Percy Anderson, May 9, 2014, pp. 1-48.

Civil Minutes-General: Case No. Cv 11-9185PA (AJWx), *InTouch Tech., Inc.* v. *VGO Commons, Inc.*, Sep. 10, 2012, 7 pages.

Defendant VGO Communications, Inc.'s Invalidity Contentions Pursuant to the Feb. 27, 2012 Civil Minute Order, May 2, 2012, 143 pages.

Defendant-Counterclaimant VGO Communications, Inc.'s Supplemental Invalidity Contentions Pursuant to the Feb. 27, 2012 Civil Minute Order, May 14, 2012, 228 pages.

Google Translation of: Innovations Report, From Research Project to Television Star: Care-O-Bot in ZDF Series, Available Online at: <http://www.innovations-report.de/specials/printa.php?id=5157>, Sep. 28, 2001, 2 pages.

Magne Charge, Smart Power for Electric Vehicles, Serial No. 75189637, Registration No. 2114006, Filing Date: Oct. 29, 1996, Aug. 26, 1997, 2 pages.

MPEG File Format Summary, Downloaded from: <http://www.fileformat.info/format/mpeg/egff.htm>, Feb. 1, 2001, pp. 1-7.

(56) References Cited

OTHER PUBLICATIONS

Nomad Scout Language Reference Manual, Nomadic Technologies, Software Version 2.7, Part No. DOC00002, Jul. 12, 1999, pp. 1-47.
Nomad Scout User's Manual, Nomadic Technologies, Software Version 2.7, Part No. DOC00004, Jul. 12, 1999, pp. 1-59.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Picture Tel Adds New Features and Functionality to its Award-Winning Live200 Desktop Videoconferencing System, PR Newswire Association, LLC, Gale, Cengage Learning, Available Online at: <http://www.thefreelibrary.com/PictureTel+Adds+New+Features+And+Functionality+To+Its+Award-Winning . . . -a019512804>, Jun. 13, 1997, 4 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
Robart I, II, III, Spawar, Systems Center Pacific, Available at: http://www.nosc.mil/robots/land/robart/robart.html, Retrieved on Nov. 22, 2010, 1998, pp. 1-8.
Screenshot Showing Google Date for Lemaire Telehealth Manual, Screenshot Retrieved on Dec. 18, 2014., pp. 1-2.
Using your Infrared Cell Phone Camera, Available Online at: <http://www.catsdomain.com/xray/about.htm>, Courtesy of Internet Wayback Machine, Jan. 30, 2010, 4 pages.
ACM Digital Library Record, "Autonomous Robots", Downloaded from: <http://dl.acm.org/citation.cfmid=591550&picked=prox&cfid=360891374&cftoken=35225929>, vol. 11, Issue 1, Jul. 2001, 2 pages.
Activemedia, Inc.,"Saphira Software Manual", Saphira Version 5.3, ActiveMedia, Inc., 1997, 105 pages.
Activmedia Robotics,"Pioneer 2/PeopleBot TM", Operations Manual, Version 9, Oct. 2001, 78 pages.
Adams, Chris, "Simulation of Adaptive Behavior (SAB'02)", Mobile Robotics Research Group, The Seventh International Conference, retrieved on Jan. 22, 2014, Available Online at: <http://www.dai.ed.ac.uk/groups/mrg/MRG.html>, Aug. 4-11, 2002, 1 page.
Ando et al., "A Multimedia Self-service Terminal with Conferencing Functions", Robot and Human Communication, RO-MAN'95, Tokyo, Proceedings of 4th IEEE International Workshop, Jul. 5-7, 1995, pp. 357-362.
Android Amusement Corp., "What Marketing Secret Renting Robots from Android Amusement Corp!", (Advertisement), 1982, 1 page.
Apple Inc.,"I Phone", iPhone Series, XP002696350, Sep. 21, 2012, pp. 1-29.
Applebome, Peter, "Planning Domesticated Robots for Tomorrow's Household", New York Times, Available Online at <http://www.theoldrobots.com/images17/dc17.JPG>, Mar. 4, 1982, 1 page.
Bar-Cohen et al., "Virtual Reality Robotic Telesurgery Simulations using MEMICA Haptic System", Proceedings of SPIE's 8th Annual International Symposium on Smart Structures and Materials, Mar. 5-8, 2001, pp. 1-7.
Barrett, Rick, "Video Conferencing Business Soars as Companies Cut Travel; Some Travel; Cuts Are Permanent", Available Online at: <http://www.ivci.com/international_videoconferencing_news_videoconferencing_news_19.html>, May 13, 2002, 2 pages.
Bartholomew, "Pharmacy Apothecary", Available Online at: <http://classes.bnf.fr/ema/grands/034.htm>, Retrieved on Jul. 26, 2012, pp. 1-2.
Bauer et al., "Remote Telesurgical Mentoring: Feasibility and Efficacy", IEEE, Proceedings of the 33rd Hawaii International Conference on System Sciences, 2000, pp. 1-9.
Bauer, Jeffreyc. , "Service Robots in Health Care: The Evolution of Mechanical Solutions to Human Resource Problems", Bon Secours Health System Inc., Technology Early Warning System(TEWS), Future of Service Robots in Health Care, Jun. 2003, pp. 1-10.
Bischoff, Rainer, "Design Concept and Realization of the Humanoid Service Robot HERMES", Field and Service Robotics, Springer, London, 1998, pp. 485-492.
Blackwell, Gerry, "Video: A Wireless LAN Killer App?", Available Online at: <http://www.wi-fiplanet.com/columns/article.php/1010261/Video-A-Wireless-LAN-Killer>, Apr. 16, 2002, 4 pages.
Blaer et al., "TopBot: Automated Network Topology Detection with a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brenner, Pablo, "A Technical Tutorial on the IEEE 802.11 Protocol", BreezeCOM Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing", Critical Care Med., vol. 32, No. 1, Jan. 2004, pp. 31-38.
Brooks, Rodney, "A Robust Layered Control System for a Mobile Robot", IEEE, Journal of Robotics and Automation, vol. 2, No. 1, Mar. 1986, pp. 14-23.
Brooks, Rodneya. , "Flesh and Machines: How Robots will Change us", Available Online at: <http://dl.acm.org/citation.cfmid=560264&preflayout=flat%25202%2520of- >, Feb. 2002, 3 pages.
Celi et al., "The eICU: It's Not Just Telemedicine", Critical Care Medicine vol. 29, No. 8 (Supplement), Aug. 2001, pp. 183-189.
Cheetham et al., "Interface Development for a Child's Video Conferencing Robot", Available Online at: <www.ryerson.ca/pebbles/publications/paper-iea200hfes-last.pdf>, 2000, 4 pages.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc., Jan. 1999, pp. 205-206.
Cleary et al., "State Of The Art in Surgical Robotics: Clinical Applications and Technology Challenges", Feb. 24, 2002, pp. 1-26.
Robot User's Manual, Describing the Nomad Scout, Carnegie Mellon University, Feb. 1, 2001, 11 pages.
CNN, "Floating 'Droids' to Roam Space Corridors of the Future", Available Online at <http://edition.cnn.com/2000/TECH/space/01/12/psa/>, Jan. 12, 2000, 3 pages.
cnn.com, "Paging Dr.Robot: Machine Helps Doctors with Patients", Sep. 30, 2003, 3 pages.
Crowley, Susanl. , "Hello to our Future", AARP Bulletin, Available Online at: <http://www.cs.cmu.ed/-nursebot/web/press/aarp 99_14/millennium.html>, Jan. 2000, 12 pages.
Kaplan et al., "An Internet Accessible Telepresence", Multimedia Systems Journal, vol. 5, 1996, 7 pages.
Keller et al., "An Interface for Raven", The National Aviary's Teleconferencing Carnegie Mellon University Robot, Interaction and Visual Interface Design, School of Design, Carnegie Mellon University, 2001, 8 pages.
Khatib,"Robots in Human Environments", Proceedings International Conference on Control, Automation, Robotics, and Vision ICRACV2000, 1999, 15 pages.
Knight et al., "Active Visual Alignment of a Mobile Stereo Camera Platform", Robotics and Automation, 2000. Proceedings. ICRA '00. IEEE International Conference, vol. 4, Apr. 24-28, 2000, pp. 3203-3208.
Koenen, Rob, "MPEG-4: A Powerful Standard for Use in Web and Television Environments", (KPN Research), Downloaded from: <http://www.w3.org/Architecture/1998/06/Workshop/paper26>, Jul. 1, 1998, 4 pages.
Kurlowicz et al., "The Mini Mental State Examination (MMSE)", Try This: Best Practices in Nursing Care to Older Adults, A series from the Hartford Institute of Geriatric Nursing, Issue No. 3, Jan. 1999, 2 pages.

(56) References Cited

OTHER PUBLICATIONS

Kuzuoka et al., "Can The GestureCam be A Surrogate?", Proceedings of the Fourth European Conference on Computer-Supported Cooperative Work, 1995, pp. 181-196.

Lane, Earl, "Automated Aides", Available Online at: <http://www.cs.cum.edu/nursebot/web/press/nd4380.htm>, Oct. 17, 2000, 4 pages.

Lee et al., "A Novel Method of Surgical Instruction: International Telementoring", World Journal of Urology, vol. 16, No. 6, Dec. 1998, pp. 367-370.

Leifer et al., "VIPRR: A Virtually In Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0, 1998-2001, 104 pages.

Library of Congress,"008—Fixed-Length Data Elements (NR)", MARC 21 Format for Classification Data, Downloaded from: <http://www.loc.gov/marc/classification/cd008.html>, Jan. 2000, pp. 1-13.

Lim et al., "Control to Realize Human-Like Walking of a Biped Humanoid Robot", Systems, Man, and Cybernetics, 2000, IEEE International Conference, vol. 5, 2000, pp. 3271-3276.

Linebarger et al., "Concurrency Control Mechanisms for Closely Coupled Collaboration in Multithreaded Virtual Environments", Department of Computer Science and Engineering, Lehigh University, vol. 13, 2004, 40 pages.

Long,"Robot Navigation Technology", Available Online at <http://www.atp.nist.gov/eao/sp950-1/helpmate.htm>, Mar. 1999, 3 pages.

Luna, Nancy, "Robot a New Face on Geriatric Care", Ocregister.com, Aug. 6, 2003, 3 pages.

Mack, Michaelj. , "Minimally Invasive and Robotic Surgery", The Journal of the American Medical Association, vol. 285, No. 5, 2001, pp. 568-572.

Mair, G.M. , "Telepresence—The Technology and its Economic and Social Implications", Technology and Society, Technology and Society at a Time of Sweeping Change Proceedings, 1997 International Symposium, Jun. 20-21, 1997, pp. 118-124.

Martin, Anya, "Brighter Days Ahead", Assisted Living Today, vol. 9, Nov./Dec. 2002, pp. 19-22.

McCardle et al., "The Challenge of Utilizing New Technology in Design Education", Loughborough University, IDATER 2000, 2000, pp. 122-127.

Meng et al., "E-Service Robot in Home Healthcare", Proceedings of the 2000 IEEE/RSJ, International Conference on Intelligent Robots and Systems, 2000, pp. 832-837.

Metz, Cade, "HP Labs", Available Online at <http://www.pcmag.com/article2/0,2817,1130820,00.asp>, Jul. 1, 2003, 4 pages.

Michaud, Anne, "Introducing "Nursebot"", Available Online at: <http://www.cs.cmu.edu/nursebot/web/press/globe301/index.html>, 2001, 4 pages.

Microsoft Corporation, Inc.,"Microsoft NetMeeting 3 Features excerpt from Official Microsoft NetMeeting 3.0 Book", Available Online at: <http://technet.microsoft.com/en-us/library/cc723477.aspx>, 2012, 6 pages.

Minsky, Marvin, "Telepresence", OMNI Magazine, Jun. 1980, 6 pages.

Montemerlo,"Telepresence: Experiments in Next Generation Internet", Available Online at <http://www.ri.cmu.edu/creative/archives.htm>, Oct. 20, 1998, 3 pages.

Murphy, Robinr. , "Introduction to AI Robotics", A Bradford Book, The MIT Press, Cambridge, Massachusetts, London, England, 2000, 487 pages.

Nakajima et al., "A Multimedia Teleteaching System using an Electronic Whiteboard for Two Way Communication of Motion Videos and Chalkboards", Robot and Human Communication, 1993, Proceedings, 2nd IEEE International Workshop, 1993, pp. 436-441.

Nakazato et al., "Group-based Interface for Content-based Image Retrieval", Proceedings of the Working Conference on Advanced Visual Interfaces, 2002, pp. 187-194.

Nakazato et al., "ImageGrouper: A Group-Oriented User Interface for Content-Based Image Retrieval and Digital Image Arrangement", Journal of Visual Languages & Computing, vol. 14, No. 4, Aug. 2003, pp. 45-46.

Nersc,"Berkeley Lab's RAGE Telepresence Robot Captures R&D100 Award", Available Online at: <https://www.nersc.gov/news-publications/news/nersc-center-news/2002/berkeley-lab-s-rage-telepresence-robot-captures-r-and-d100-award/>, Jul. 2, 2002, pp. 1-2.

Nomadic Technologies Inc.,"Nomad XR4000 Hardware Manual", Release 1.0, Mar. 1999, 34 pages.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R—Experimental Evaluation", Proceedings of the 2000 IEEE/RSJ International Conference on Intelligent Robots and Systems, vol. 1, 2000, pp. 175-180.

Ogata et al., "Emotional Communication Robot: WAMOEBA-2R—Emotion Model and Evaluation Experiments", Proceedings of the International Conference on Humanoid Robots, 2000, pp. 1-16.

Oh et al., "Autonomous Battery Recharging for Indoor Mobile Robots", Proceedings of Australian Conference on Robotics and Automation, 2000, pp. 1-6.

Ojha, Anandk. , "An application of Virtual Reality in Rehabilitation", Proceedings of the 1994 IEEE Southeastcon 94. Creative Technology Transfer—A Global Affair, Apr. 1994, pp. 4-6.

Osborn, Jim, "Quality of Life Technology Center", QoLT Research Overview: A National Science Foundation Engineering Research Center, Carnegie Mellon University of Pittsburgh, 2 pages.

Panusopone et al., "Performance Comparison of MPEG-4 and H.263+ for Streaming Video Applications", Circuits Systems Signal Processing, vol. 20, No. 3, 2001, pp. 293-309.

Paulos et al., "A World Wide Web Telerobotic Remote Environment Browser", Available Online at: <http://www.w3.org/Conferences/WWW4/Papers/326/>, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos, Ericj. , "Personal Tele-Embodiment", Dissertation, Doctor of Philosophy in Computer Science in the Graduate Division of the University of California at Berkeley, 2001, 282 pages.

Paulos, Ericj. , "Personal Tele-Embodiment", OskiCat Catalog Record, UCB Library Catalog, 2001, 3 pages.

Paulos et al., "Personal Tele-Embodiment", Chapter 9 in Goldberg, et al., Ed. "Beyond Webcams", MIT Press, Jan. 4, 2002, pp. 155-167.

Paulos, Ericj. , "Personal Tele-Embodiment", Introductory and Cover Pages from 2001 Dissertation Including Contents Table, Together With E-Mails Relating Thereto From UC Berkeley Libraries, as Shelved at UC Berkeley Engineering Library (Northern Regional library Facility), May 8, 2002, 25 pages, Including 4 pages of E-Mails.

Paulos et al., "PROP: Personal Roving Presence", ACM:CHI Proceedings of CHI '98, 1998, 8 pages.

Paulos et al., "Social Tele-Embodiment: Understanding Presence", Autonomous Robots, vol. 11, Issue 1, Kluwer Academic Publishers, Jul. 2001, pp. 87-95.

Paulos et al., "Ubiquitous Tele-Embodiment: Applications and Implications", International Journal of Human Computer Studies, vol. 46, No. 6, Jun. 1997, pp. 861-877.

Paulos et al., "Video of PRoP 2 at Richmond Field Station", Available Online at: <www.prop.org>, Printout of Home Page of Website and two-page Transcript of the audio portion of said PRoP Video, May 2001, pp. 1-2.

Picturetel Corporation,"PictureTel Live200 for Windows NT Product Guide", 1997, 63 pages.

(56) References Cited

OTHER PUBLICATIONS

Pin et al., "A New Family of Omnidirectional and Holonomic Wheeled Platforms for Mobile Robots", IEEE Transactions on Robotics and Automation, vol. 10, No. 4, Aug. 1994, pp. 480-489.
Piquepaille, Roland, "How New Technologies are Modifying our Way of Life", Roland Piquepaille's Technology Trends, This Blog and its RSS Feed are Moving, Oct. 31, 2004, 2 pages.
Radvision, "Making Sense of Bandwidth the NetsenseWay", Network Congestion in Unmanaged Networks Bandwidth Estimation and Adaptation Techniques, White Paper, Radvision's Netsense Technology, 2010, 7 pages.
Reynolds et al., "Review of Robotic Telemedicine Utilization in Intensive Care Units (ICUs)", 11th Annual ATA Symposium, Tampa, Florida, 2011, 1 page.
Roach, Adam, "Automatic Call Back Service in SIP", Internet Engineering Task Force, Internet Draft, Category: Informational, Mar. 2000, 8 pages.
Rovetta et al., "A New Telerobotic Application: Remote Laparoscopic Surgery Using Satellites and optical fiber Networks for Data Exchange", International Journal of Robotics Research, vol. 15, No. 3, Jun. 1, 1996, pp. 267-279.
Roy et al., "Towards Personal Service Robots for the Elderly", Workshop on Interactive Robots and Entertainment (WIRE 2000), vol. 25, Available Online at <http://www.ri.cmu.edu/pb_files/pub2/roy_nicholas_2000_1/roy_nicholas_2000_1.pdf>, Apr. 30-May 1, 2000, 7 pages.
Sachs et al., "Virtual Visit: Improving Communication for Those Who Need it Most", Studies in Health Technology and Informatics, Medicine Meets Virtual Reality 11, vol. 94, 2003, pp. 302-308.
Salemi et al., "MILO: Personal Robot Platform", IEEE/RSJ International Conference on Intelligent Robots and Systems, Aug. 2005, pp. 4089-4094.
Sandt et al., "Perceptions for a Transport Robot in Public Environments", Proceedings of the 1997 IEEE/RSJ International Conference on Intelligent Robots and Systems, vol. 1, Sep. 7-11, 1997, pp. 360-365.
Sawyer, Robertj., "Inventing the Future: 2000 Years of Discovery", Available Online at: <http://www.sfwriter.com/pritf.htm>, Jan. 2, 2000, 2 pages.
Schaeffer et al., "Care-O-BotTM: The Concept of a System for Assisting Elderly or Disabled Persons in Home Environments", Proceedings of the 24th Annual Conference of the IEEE Industrial Electronics Society, vol. 4, 1998, pp. 2476-2481.
Schultz et al., "Web Interfaces for Mobile Robots in Public Places", IEEE Robotics & Automation Magazine, vol. 7, No. 1, Mar. 2000, pp. 48-56.
Shimoga et al., "Touch and Force Reflection for Telepresence Surgery", Proceedings of the 16th Annual International Conference of the IEEE Engineering in Medicine and Biology Society, Nov. 1994, pp. 1049-1050.
Siegwart et al., "Interacting Mobile Robots on the Web", Proceedings of the 1999 IEEE International Conference on Robotics and Automation, May 1999, pp. 1-7.
Simmons et al., "Xavier: An Autonomous Mobile Robot on the Web", IEEE Robotics and Automation Magazine, 1999, pp. 43-48.
Stephenson, Gary, "Dr. Robot Tested at Hopkins", Available Online at: <http://www.hopkinsmedicine.org/press/2003/august/030805.htm>, Aug. 5, 2003, 2 pages.
Stoianovici et al., "Robotic Tools for Minimally Invasive Urologic Surgery", Complications of Urologic Laparoscopic Surgery: Recognition, Management and Prevention, Dec. 2002, 17 pages.
Suplee, Curt, "Mastering the Robot", The Washington Post, Washington Post Staff Writer, Sep. 17, 2000, 5 pages.
Tahboub et al., "Dynamics Analysis and Control of a Holonomic Vehicle with Continuously Variable Transmission", Transactions of the ASME, Journal of Dynamic Systems, Measurement and Control, vol. 124, Mar. 2002, pp. 118-126.
Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.
Theodosiou et al., "MuLVAT: A Video Annotation Tool Based on XML-Dictionaries and Shot Clustering", Part II, 19th International Conference, Artificial Neural Networks-ICANN 2009, Sep. 14-17, 2009, pp. 913-922.
Thrun et al., "Probabilistic Algorithms and the Interactive Museum Tour-Guide Robot Minerva", International Journal of Robotics Research, vol. 19, 2000, pp. 1-35.
Time, Lists, "Office Coworker Robot", Best Inventions of 2001, Available Online at: <http://content.time.com/time/specials/packages/article/0,28804,1936165_1936255_1936640,00.html>, Nov. 19, 2001, 2 pages.
Tipsuwan et al., "Gain Adaptation of Networked Mobile Robot to Compensate QoS Deterioration", 28th Annual Conference of the Industrial Electronics Society, vol. 4, Nov. 5-8, 2002, pp. 3146-3151.
Tsui et al., "Exploring Use Cases for Telepresence Robots", 6th ACM/IEEE International Conference on Human-Robot Interaction (HRI), Mar. 2011, pp. 11-18.
Tyrrell et al., "Teleconsultation in Psychology: The Use of Videolinks for Interviewing and Assessing Elderly Patients", Age and Ageing, vol. 30, No. 3, May 2001, pp. 191-195.
Tzafestas et al., "VR-Based Teleoperation of a Mobile Robotic Assistant: Progress Report", Technical Report DEMO 2000/13, Institute of Informatics and Telecommunications, National Center for Scientific Research "Demokritos", Nov. 2000, pp. 1-23.
Umass Lowell Robotics Lab, "Robotics Lab @ UMASS Lowell", Brochure, 2011, 2 pages.
Urquhart, Kim, "InTouch's Robotic Companion 'Beams Up' Healthcare Experts", Medical Device Daily, vol. 7, No. 39, Feb. 27, 2003, pp. 1-4.
Video Middleware Cookbook, "H.350 Directory Services for Multimedia", 2 pages.
Weaver et al., "Monitoring and Controlling using the Internet and Java", Proceedings of the 25th Annual Conference of the IEEE Industrial Electronics Society, vol. 3, 1999, pp. 1152-1158.
Weiss et al., "Pebbles: A Personal Technology for Meeting Education, Social and Emotional Needs of Hospitalised Children", Personal and Ubiquitous Computing, vol. 5, No. 3, Aug. 2001, pp. 157-168.
Weiss et al., "Telework and Video-Mediated Communication: Importance of Real-Time, Interactive Communication for Workers with Disabilities", Available Online at: <http://www.telbotics.com/research_3.htm>, Retrieved on Nov. 23. 2010, 3 pages.
West et al., "Design of Ball Wheel Mechanisms for Omnidirectional Vehicles with Full Mobility and Invariant Kinematics", Journal of Mechanical Design, vol. 119, Jun. 1997, pp. 153-161.
Yamasaki et al., "Applying Personal Robots and Active Interface to Video Conference Systems", 6th International Conference on Human Computer Interaction, vol. B, 1995, pp. 243-248.
Yamauchi, Brian, "PackBot: A Versatile Platform for Military Robotics", Proceedings of SPIE for Military Robotics, 2004, pp. 228-237.
Yong et al., "Robot Task Execution with Telepresence using Virtual Reality Technology", 1998 International Conference on Mechatronic Technology, Nov. 30-Dec. 2, 1998, pp. 1-8.
Zambroski, James, "CMU, Pitt Developing 'Nursebot'", Available Online at: <http://www.cs.cmu.edu/~nursebot/web/press/tribunereview.html>, Oct. 27, 2000, 3 pages.
Zamrazil, Kristie, "Telemedicine in Texas: Public Policy Concerns", Focus Report, House Research Organization, Texas House of Representatives, No. 76-22, May 5, 2000, pp. 1-16.
Zipperer, Lorri, "Robotic Dispensing System", ISMP Medication Safety Alert!, vol. 4, No. 17, Aug. 25, 1999, 2 pages.
Zorn, Benjaming., "Ubiquitous Telepresence", Department of Computer Science, University of Colorado, 1996, 13 pages.
Dalton, Barnaby, "Techniques for Web Telerobotics", PHD Thesis, University of Western Australia, Available Online at: <http://telerobot.mech.uwa.edu.au/information.html>, <ttp://catalogue.library.uwa.edu.au/search>, 2001, 243 pages.

(56) References Cited

OTHER PUBLICATIONS

Dario et al., "A Robot Workstation for Diagnosis and Physical Therapy", IEEE Catalog No. 88TH0234-5, Centro "E. Piaggio" University of Pisa, Italy, 1989, pp. 67-72.

Davies, Brian, "Robotics in Minimally Invasive Surgery", Mechatronics in Medicine Lab, Dept Mechanical Engineering, Imperial College, London SW7 2BX, The Institution of Electrical Engineers, IEE, Savoy Place, London WC2R OBL, Uk, 1995, pp. 1-2.

Davis, Erik, "Telefriend, Meet iRobot, the Smartest Webcam on Wheels", Wired Magazine, Issue 8.09, Available Online at: <http://www.wired.com/wired/archive/8.09/irobot.html?pg=1&topic=&topic_set=>, Sep. 2000, 3 pages.

Dean et al., "1992 AAAI Robot Exhibition and Competition", Articles, AI Magazine, vol. 14, No. 1, 1993, 15 pages.

Digiorgio, James, "Is Your Emergency Department of the Leading Edge?", Chicago Hospital News, vol. 2, No. 12, 2005, 3 pages.

Dudenhoeffer et al., "Command and Control Architectures for Autonomous Micro-Robotic Forces", FY00 Project Report, Idaho National Engineering and Environmental Laboratory Human Systems Engineering and Sciences Department, Idaho Falls, Apr. 2001, 43 pages.

Elepresence Research, Inc.,"The Telepresence Mobile Robot System", Available Online at: <http://www.telepresence.com/telepresenceresearch/TELEROBOT/>, Feb. 20, 1995, 3 pages.

Elhajj et al., "Real-Time Haptic Feedback in Internet-based Telerobotic Operation", IEEE International Conference on Electro/Information Technology, Available Online at <http://www.egr.msu.edu/~ralab-web/cgi_bin/internet-teleoperation.php>, Jun. 2000, 10 pages.

Elhajj et al., "Supermedia in Internet-Based Telerobotic Operations", Management of Multimedia on the Internet Lecture Notes in Computer Science, vol. 2216, Springer-Verlag Berlin Heidelberg, 2001, 4th IFIP/IEEE International Conference on Management of Multimedia Networks and Services, MMNS 2001 Chicago, IL, USA, 2001 Proceedings, Oct. 29-Nov. 1, 2001, pp. 359-372.

Elhajj et al., "Synchronization and Control of Supermedia Transmission Via the Internet", Proceedings of 2001 International Symposium on Intelligent Multimedia Video and Speech Processing, Hong Kong, May 2-4, 2001, pp. 320-323.

Ellison et al., "Telerounding and Patient Satisfaction Following Surgery", 2004, pp. 523-530.

Evans et al., "HelpMate: The Trackless Robotic Courier", PYXIS HelpMate®, 2007, 3 pages.

Fels et al., "Developing a Video-Mediated Communication System for Hospitalized Children", Telemedicine Journal, vol. 5, No. 2, 1999, 30 pages.

Fetterman, Davidm. , "Videoconferencing over the Internet", Qualitative Health Journal, vol. 7, Issue 1, 2001, 8 pages.

Fiorini et al., "Health Care Robotics: A Progress Report", IEEE International Conference on Robotics and Automation, Apr. 20-25, 1997, pp. 1271-1276.

Fong, Terrence, "Collaborative Control: A Robot-Centric Model for Vehicle Teleoperation", Doctoral Dissertation, Technical Report CMU-RI-TR-01-34, Robotics Institute, Carnegie Mellon University, Nov. 2001, 197 pages.

Fulbright et al., "SWAMI: An Autonomous Mobile Robot for Inspection of Nuclear Waste of Storage Facilities", Autonomous Robots, 2, 1995, pp. 225-235.

Gaidioz et al., "Synchronizing Network Probes to Avoid Measurement Intrusiveness with the Network Weather Service", Proceedings of the Ninth International Symposium on High-Performance Distributed Computing, 2000, pp. 147-154.

Garner et al., "The Application of Telepresence in Medicine", BT Technology Journal, vol. 15, No. 4, Oct. 1, 1997, pp. 181-187.

Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.

Goldberg et al., "Collaborative Teleoperation Via the Internet", IEEE International Conference on Robotics and Automation (ICRA), vol. 2, San Francisco, California, 2000, pp. 2019-2024.

Goldberg et al., "Desktop Teleoperation Via the World Wide Web", Robotics and Automation, 1995 Proceedings., 1995 IEEE International Conference, vol. 1, May 21-27, 1995, pp. 654-659.

Goldberg, "More Online Robots: Robots that Manipulate", Available Online at: <http://ford.ieor.berkeley.edu/ir/robots_a2.html>, Aug. 2001, 2 pages.

Goldenberg et al., "Telemedicine in Otolaryngology", American Journal of Otolaryngology, vol. 23, No. 1, 2002, pp. 35-43.

Goldman, Lea, "Machine Dreams", Available Online at: <http://www.forbes.com/global/2002/0527/043.html>, May 27, 2002, 5 pages.

Gostai,"Gostai Jazz: Robotic Telepresence", Available Online at <http://www.gostai.com>, 4 pages.

Gump, Michaeld. , "Robot Technology Improves VA Pharmacies", U.S. Medicine Informational Central, Jul. 2001, 3 pages.

Hameed et al., "A Review of Telemedicine", Journal of Telemedicine and Telecare., vol. 5, Supplement 1, 1999, pp. 103-106.

Han et al., "Construction of an Omnidirectional Mobile Robot Platform based on Active Dual-Wheel Caster Mechanisms and Development of a Control Simulator", Kluwer Acedemic Publishers, vol. 29, Nov. 2000, pp. 257-275.

Handley et al., "RFC 2327—SDP: Session Description Protocol", Available Online at: <http://www.faqs.org/rfcs/rfc2327.html>, Apr. 1998, 22 pages.

Hanebeck et al., "Roman: A Mobile Robotic Assistant for Indoor Service Applications", Intelligent Robots and Systems, 1997 IROS '97, Proceedings of the 1997 IEEE/RSJ International Conference on Intelligent Robots and Systems, vol. 2, Sep. 7-11, 1997, pp. 518-525.

Harmo et al., "Moving Eye-Interactive Telepresence over Internet with a Ball Shaped Mobile Robot", Available Online at: <http://automation.tkk.fi/files/tervetaas/MovingEye4.pdf>, 2000, 6 pages.

Haule et al., "Control Scheme for Delayed Teleoperation Tasks", Communications, Computers, and Signal Processing, 1995. Proceedings., IEEE Pacific Rim Conference, May 17-19, 1995, pp. 157-160.

Hees, Williamp. , "Communications Design for a Remote Presence Robot", CSCI E-131b, Final Project, Jan. 14, 2002, 12 pages.

Herias et al., "Flexible Virtual and Remote Laboratory for Teaching Robotics", FORMATEX 2006, Proceedings of Advance in Control Education Madrid, Spain, Jun. 2006, pp. 1959-1963.

Holmberg, "Development of a Holonomic Mobile Robot for Mobile Manipulation Tasks", The Robotics Laboratory, Computer Science Department, Stanford University, Stanford, California, USA, vol. 19, No. 11, Nov. 2000, pp. 1066-1074.

Ishiguro et al., "Integrating a Perceptual Information Infrastructure with Robotic Avatars: A Framework for Tele-Existence", Intelligent Robots and Systems, 1999. IROS '99. Proceedings. 1999 IEEE/RSJ International Conference, vol. 2, 1999, pp. 1032-1038.

Ishihara et al., "Intelligent Microrobot DDS (Drug Delivery System) Measured and Controlled by Ultrasonics", Intelligent Robots and Systems '91. Intelligence for Mechanical Systems, Proceedings IROS '91. IEEE/RSJ International Workshop, vol. 2, Nov. 3-5, 1991, pp. 1145-1150.

ITU,"Call Completion Supplementary Services for H.323", ITU-T, Telecommunication Standardization Sector of ITU, H.450.9, Series H: Audiovisual And Multimedia Systems, Nov. 2000, 63 pages.

ITU,"Call Intrusion Supplementary Service for H.323", ITU-T, Telecommunication Standardization Sector of ITU, H.450.11, Series H: Audiovisual And Multimedia Systems, Mar. 2001, 59 pages.

ITU,"Packet-Based Multimedia Communications Systems", ITU-T, Telecommunication Standardization Sector of ITU, H.323, Series H: Audiovisual and Multimedia Systems, Feb. 1998, 128 Pages.

ITU,"Transmission of Non-Telephone Signals: A Far End Camera Control Protocol for Videoconferences Using H.224", ITU-T, Telecommunication Standardization Sector of ITU, H.281, Nov. 1994, 12 pages.

Ivanova, Natali, "Master's thesis: Internet based Interface for Control of a Mobile Robot", Department of Numerical Analysis and Computer Science, 2003, 59 pages.

Jacobs et al., "Applying Telemedicine to Outpatient Physical Therapy", AMIA, Annual Symposium Proceedings, 2002, 1 page.

(56) References Cited

OTHER PUBLICATIONS

Jenkins et al., "Telehealth Advancing Nursing Practice", Nursing Outlook, vol. 49, No. 2, Mar. 2001, pp. 100-105.
Johanson, Mathias, "Supporting Video-Mediated Communication Over the Internet", Department of Computer Engineering, Chalmers University of Technology, Gothenburg, Sweden, 2003, 222 pages.
Jouppi et al., "BiReality: Mutually-Immersive Telepresence", Multimedia '04 Proceedings of the 12th Annual ACM International Conference on Multimedia, Oct. 10-16, 2004, pp. 860-867.
Jouppi et al., "First Steps Towards Mutually-Immersive Mobile Telepresence", CSCW '02 Proceedings of the 2002 ACM conference on Computer Supported Cooperative Work, Nov. 16-20, 2002, pp. 354-363.
Kanehiro et al., "Virtual Humanoid Robot Platform to Develop Controllers of Real Humanoid Robots without Porting", Intelligent Robots and Systems, 2001. Proceedings. 2001 IEEE/RSJ International Conference, vol. 2, 2001, pp. 1093-1099.

* cited by examiner

SYSTEMS AND METHODS FOR NETWORK-BASED COUNSELING

RELATED APPLICATIONS

This application is a continuation-in-part of U.S. patent application Ser. No. 13/372,365 filed Feb. 13, 2012 and titled "Methods and Systems for Online Counseling Sessions and Clinics," which claims priority to U.S. Provisional Patent Application Ser. No. 61/443,657 filed Feb. 16, 2011 and titled, "Method and System for Online Psychotherapy Sessions and Clinics," and to U.S. Provisional Patent Application Ser. No. 61/545,992 filed Oct. 11, 2011 and titled, "Methods and Systems for Online Counseling Sessions and Clinics."

BACKGROUND OF THE INVENTION

1. Field of the Invention

The invention relates generally to methods and systems for conducting counseling sessions. More particularly, the invention relates to methods and systems for counseling sessions and clinics conducted remotely, such as over the Internet and/or via satellite using WIFI as well as other web-based technologies. In addition, the invention relates to methods and systems for conducting remote counseling sessions by means of various mobile devices as well as collecting biofeedback and/or biometric data via biometric devices configured to interface with an associated hub, network and/or portal to enhance the efficacy and value of the remote counseling sessions as well as to authenticate the identity of a client.

2. Background and Related Art

Counseling is a means by which people can gain valuable advice from experts. Typically, psychological, psychiatric, medical, genomic, life, business, mechanical, wedding, academic, legal, or other forms of counseling, occur in an expert's office or place of business. In this setting, the expert controls the environment in which the counseling takes place. The client generally schedules an appointment with the expert and then attends the session with the expert at the appointed time. The client and the expert communicate during the counseling session, which generally may include the client conveying information to the expert about the client's needs and/or condition. The information about the client's needs and/or condition may include details of the client's experiences, feelings, history, condition and other extremely personal information. Upon receiving this information, the expert may then counsel the client depending on the nature of the information revealed to the expert by the client. Some experts provide set training courses to individuals in addition to or in lieu of tailored counseling sessions. Some counseling sessions occur in which there are multiple clients and/or multiple experts, which are sometimes called group counseling.

BRIEF SUMMARY OF THE INVENTION

The invention relates generally to methods and systems for conducting counseling sessions. More particularly, the invention relates to methods and systems for counseling sessions and clinics conducted remotely, such as networks based on satellites, microwave, Bluetooth, or over the Internet and/or via satellite or WIFI as well as other web-based technologies. In addition, the invention relates to methods and systems for conducting remote counseling sessions by means of various mobile devices as well as biofeedback and/or biometric data collected via biometric devices configured to interface with an associated network and/or portal to enhance the efficacy and value of the remote counseling sessions.

Accordingly, methods and systems for online counseling sessions conducted over the Internet are disclosed. In some configurations, a method for remotely conducting counseling sessions between a client and an expert using an IP-based network includes providing a website accessible to the network wherein the expert and a client both have access to the website. In such configurations, upon accessing and logging into the website, the client is permitted to search a database for online experts and select an appropriate expert for a counseling session. In some configurations, the client initially completes various intake and/or registration forms in a virtual waiting room, wherein such forms are customized per the relevant expert. The method continues as an expert remotely conducts a counseling session with the client via remote means, including video conferencing. Following the counseling session, the client is automatically returned to the virtual waiting room and provided with subsequent counseling based options.

In some configurations, the methods of the present invention are directed to expert marketing capabilities and/or strategies. In other configurations, the methods of the present invention are directed to client scheduling or calendaring for counseling sessions, including synchronization with Outlook™, Gmail™, iCal™ or other electronic and/or web-based calendaring systems or programs and synchronizing interfacing and/or integration with EMR, PHR, OEM vendors via API, HL7 interfaces/messages and FHIR interfaces. In still other configurations, email, text, SMS messaging, instant messaging and the like are employed to confirm appointments and/or provide reminders of upcoming appointments, to customize general information presented to individual clients, to secure client access to personalized reports and documentation generated by the expert which, in some configurations, are accessible to individual client and expert only, to provide access to products for purchase selected by the expert for the client, to provide a full accounting and payment system for experts as well as clients, to facilitate client rating and feedback on the expert relative to services rendered or previously provided, and many other aspects as further disclosed herein.

In some configurations, the network and associated portal employed or used to practice various configurations of the invention may further be utilized to provide training or educational services for experts categorized by field, topic, and/or experience level. Accordingly, in various configurations, the methods and systems of the present invention provide resources for both clients seeking counseling as well as experts seeking additional education or training. In all such configurations, various forms of electronic communication can be used to supplement online counseling sessions and/or training/education such as on demand products, live webcast products, electronic documents or print products, electronic media, facsimile and other forms of communication. Experts seeking to use the systems and methods of the present invention can search for and find additional training and/or educational serves from other experts available through the service in much the same way that clients seeking counseling can find specific experts in a relevant field.

Some configurations enable clients to access counseling services when and where it is most convenient for them, and increase the flexibility of counseling by offering 24-hour availability for pay-per-minute, pre-determined amounts for predetermined amounts of time, other pay-per-view sessions or with possibly no charge to the client. Some configurations allow experts in any stage of their practice to provide more support to existing clients and to procure new clients regardless of geographical limitations.

In some configurations, when scheduling an appointment, a client logs in to the expert's website or other type of Internet portal and accesses a scheduling calendar which displays the available counseling sessions. According to some configurations, the expert has the ability to alter the calendar so that the view is client dependent. By way of example, in some embodiments the calendar may be manipulated so that fewer "available" counseling sessions are displayed for these clients. In some configurations, one or more discrete or otherwise independent clinics can also employ the teachings disclosed herein to interface and/or coordinate with one another to simplify inter-office scheduling as well as streamlining other document and/or record keeping as well as a host of services that can be offered to a range of clients. In some configurations, if an expert finds himself or herself without any clients, e.g., due to cancellations, the inability of clients to travel to the office due to severe weather, etc., that expert can place an "available" icon on the homepage so that clients desiring counseling know that they can have immediate access without consulting the calendar.

In some configurations, group counseling sessions can be given. In some configurations, all clients can see the expert and the expert can see all of the clients at the same time on smaller images on one screen. In such configurations, the expert can assess the demeanor of the clients as they interact. In some configurations, the clients will be able to see each other and/or hear each other. In some configurations, online group counseling can be augmented by occasional private conversations. In some further configurations, the client or the expert may press a button sending an indication that they desire a private conversation, the expert may then excuse himself or herself from the group discussion and engage in a private conversation shielded from the view and hearing of the other group members.

In some configurations, a hold type button (or a type of privacy button) is provided which allows the client and expert or expert's staff to pause or temporarily suspend a particular session or to otherwise provide the client, expert or expert's staff with an opportunity to put the session on hold without actually ending the session. In this way, the client, expert or expert's staff has the ability to interrupt the session with respect to him or herself without affecting the session relative to other uses in order to protect the client's privacy. Specifically, the client, expert or expert's staff has the ability to pause the session on his or her end so that if something in his or her environment changes, the client, expert or expert's staff can control broadcasting such changes to either the expert and/or the other members of the group, or rather has control in order to avoid such a broadcast.

In various configurations, a "take the floor" feature is offered during a group counseling session. In some configurations, an expert offers a client the opportunity to lead the discussion by illuminating an icon or reference on the screen in the appropriate location. In some embodiments an "emergency" feature is offered to clients who need emergency contact information for an expert and/or an immediate counseling session with an expert.

In some configurations, an expert, administrator or other expert can designate an assistant who has access to the systems of the present invention, including the portal. In some configurations, for example, an assistant or staff member may be a registered nurse or a practitioner's assistant. In such configurations, the assistant is capable of meeting with and/or pre-screening clients. Such configurations further contemplate one or more, including multiple, assistants or staff members, some of whom work out of different clinics, working with any number of clients for, in connection with or on behalf of a single practitioner. In this way, one practitioner can be affiliated with multiple clinics and provide counseling or other treatment to multiple clients efficiently and effectively. In some configurations, multiple assistants or staff members associated with multiple clinics are associated with multiple practitioners. In such configurations, the assistants or staff members may have limited access to client information to preserve various privacy aspects and in some configurations the assistants must be licensed in order to provide assistance.

In some configurations, physiological, biometric, biofeedback or psychological sensor data from sensors that are attached to or in sensing range of a client may transmit sensor data to an expert services platform from which the data may be passed on to an expert in raw form or may be converted, correlated and otherwise modified or transformed to better serve a diagnostic or other purpose.

Additional features and advantages of the invention will be set forth in the description which follows, and in part will be apparent from the description, or may be learned by the practice of the present invention.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
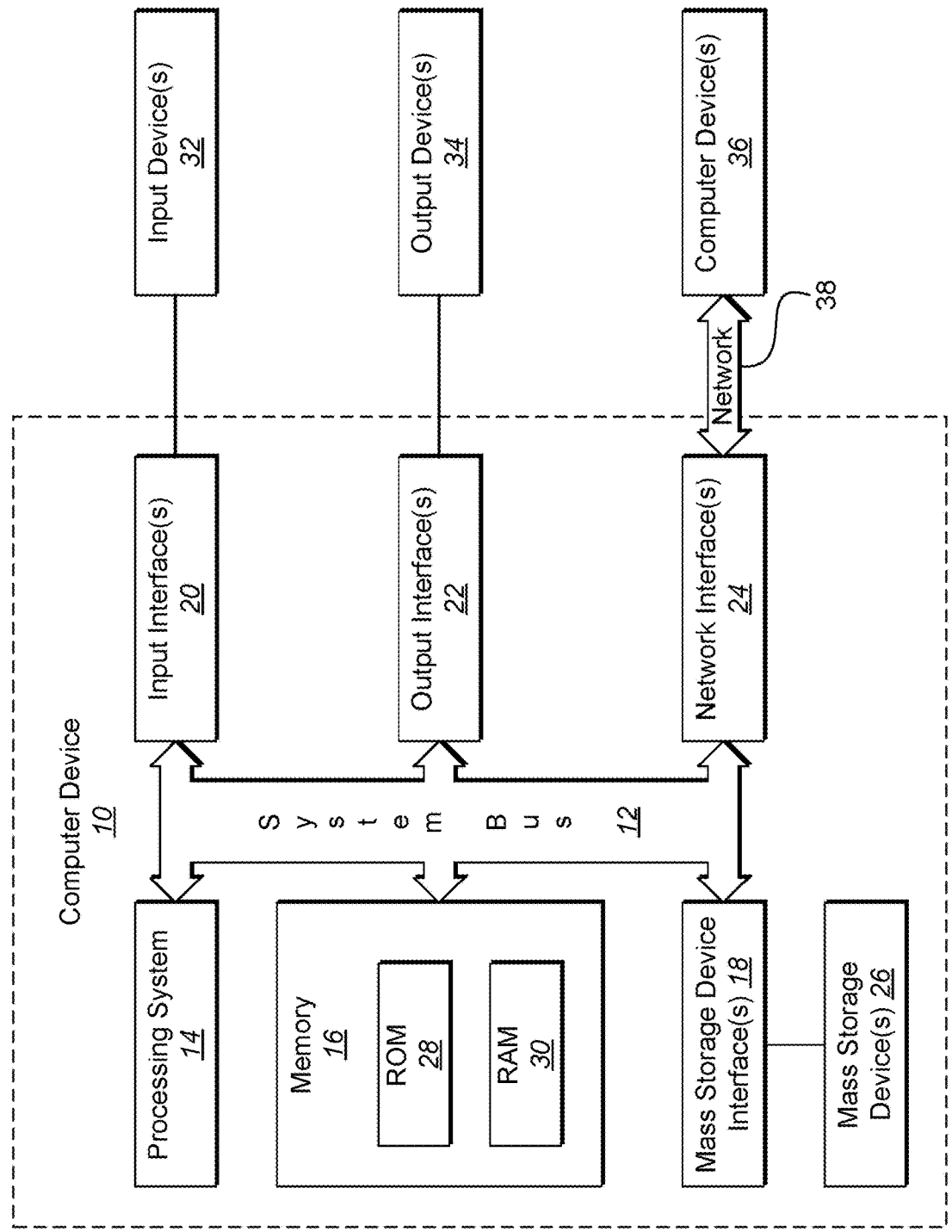
FIG. 1 shows an exemplary general-purpose computer system.

A description of embodiments of the present invention will now be given. It is expected that the present invention may take many other forms and shapes, hence the following disclosure is intended to be illustrative and not limiting, and the scope of the invention should be determined by reference to the appended claims and their equivalents.

The following description supplies specific details in order to provide a thorough understanding. Nevertheless, the skilled artisan would understand that the online counseling sessions and clinics can be implemented and used without employing these specific details. Indeed, the invention can be practiced by modifying the illustrated method and can be used in conjunction with apparatuses and/or techniques conventionally used in the industry. For example, the description focuses on providing psychotherapy counseling online. But it could be easily adapted to provide online genomics, medical, wedding, academic, veterinarian or other post-traumatic stress, mechanical, legal or other forms of counseling wherein an expert traditionally meets with his or her clients to provide advice and or associated literature or printed materials.

In understanding the scope of the present invention, the term "configured" as used herein to describe a component, section or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including," "having" and their derivatives. Also, the terms "part," "section," "portion," "member" or "element" when used in the singular can have the dual meaning of a single part or a plurality of parts. Finally, terms of degree such as "substantially," "about" and "approximately" as used herein mean a reasonable amount of deviation of the modified term such that the end result is not significantly changed.

The terms "client," "patient," "employee," "recipient," etc., may be used herein. Such terms are intended to be used synonymously and refer to a user, group of users, business, and/or other entity seeking counseling or advice via the present invention.

The terms "expert," "provider," "physician," "practitioner," "contractor," "employer," "professional," etc., may be used herein. Such terms are intended to be used synonymously and refer to an individual, a group of individuals, a business, and/or other entity that provides counseling via the present invention.

Various operations may be described as multiple discrete operations in turn, in a manner that may be helpful in understanding embodiments of the present invention; however, the order of description should not be construed to imply that these operations are order dependent.

The description may use the phrases "in an embodiment," "in some embodiments," "in various embodiments," or other similar phrase, which may each refer to one or more of the same or different embodiments. Furthermore, the terms "comprising," "including," "having," and the like, as used with respect to embodiments of the present invention, are synonymous with the definition afforded the term "comprising."

The term "etc." may be used. It should be understood that the term indicates that other examples or elements are possible. The term "etc." should not be interpreted to be limited in kind, category, or similarity to the terms that precede it, but instead indicate that there are other possible examples or elements that could be given that may or may not be wholly different from the terms that precede it.

For the purposes of the present invention, the phrase "A/B" means "A or B." For the purposes of the present invention, the phrase "A and/or B" means "(A), (B), or (A and B)." For the purposes of the present invention, the phrase "at least one of A, B, and C" means "(A), (B), (C), (A and B), (A and C), (B and C), or (A, B and C)." For the purposes of the present invention, the phrase "(A)B" means "(B) or (AB)," that is, A is an optional element.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

FIG. 1 and the corresponding discussion are intended to provide a general description of a suitable operating environment in which embodiments of the invention may be implemented. One skilled in the art will appreciate that embodiments of the invention may be practiced by one or more computing devices and in a variety of system configurations, including in a networked configuration. However, while the methods and processes of the present invention have proven to be useful in association with a system comprising a general purpose computer, embodiments of the present invention include utilization of the methods and processes in a variety of environments, including embedded systems with general purpose processing units, digital/media signal processors (DSP/MSP), application specific integrated circuits (ASIC), stand-alone electronic devices, and other such electronic environments.

Embodiments of the present invention embrace one or more computer-readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. While embodiments of the invention embrace the use of all types of computer-readable media, certain embodiments as recited in the claims may be limited to the use of tangible, non-transitory computer-readable media, and the phrases "tangible computer-readable medium" and "non-transitory computer-readable medium" (or plural variations) used herein are intended to exclude transitory propagating signals per se.

With reference to FIG. 1, a representative system for implementing embodiments of the invention includes computer device 10, which may be a general-purpose or special-purpose computer or any of a variety of consumer electronic devices. For example, computer device 10 may be a personal computer, a notebook or laptop computer, a netbook, a personal digital assistant ("PDA") or other hand-held device, a smart phone, a tablet computer, a workstation, a minicomputer, a mainframe, a supercomputer, a multi-processor system, a network computer, a processor-based consumer electronic device, a computer device integrated into another device or vehicle.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

A health data sensor may be any sensor capable of measuring or monitoring some aspect of the body including physiological, biofeedback, biometric, or psychological sensors.

Processing system 14 includes one or more processors, such as a central processor and optionally one or more other processors designed to perform a particular function or task. It is typically processing system 14 that executes the instructions provided on computer-readable media, such as on memory 16, a magnetic hard disk, a removable magnetic disk, a magnetic cassette, an optical disk, or from a communication connection, which may also be viewed as a computer-readable medium.

Memory 16 includes one or more computer-readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives and optical disk drives. A mass storage device 26 may read from and/or write to a magnetic hard disk, a removable magnetic disk, a magnetic cassette, an optical disk, or another computer-readable medium. Mass storage devices 26 and their corresponding computer-readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard, touchpad, dedicated buttons, mouse, trackball, light pen, stylus, or other pointing device, a microphone, a joystick, a game pad, a satellite dish, a scanner, a camcorder, a digital camera, health data sensors, biometric or biofeedback devices, smartphone attachments (otoscope as an example), custom design interfaces, fitness bands, watches, etc. Similarly, examples of input interfaces 20 that may be used to connect the input devices 32 to the system bus 12 include a serial port, a parallel port, a game port, a universal serial bus ("USB"), an integrated circuit, a firewire (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen, a speaker, a printer, a multi-functional peripheral, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet, LTE, GSM, etc. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Figure 2:
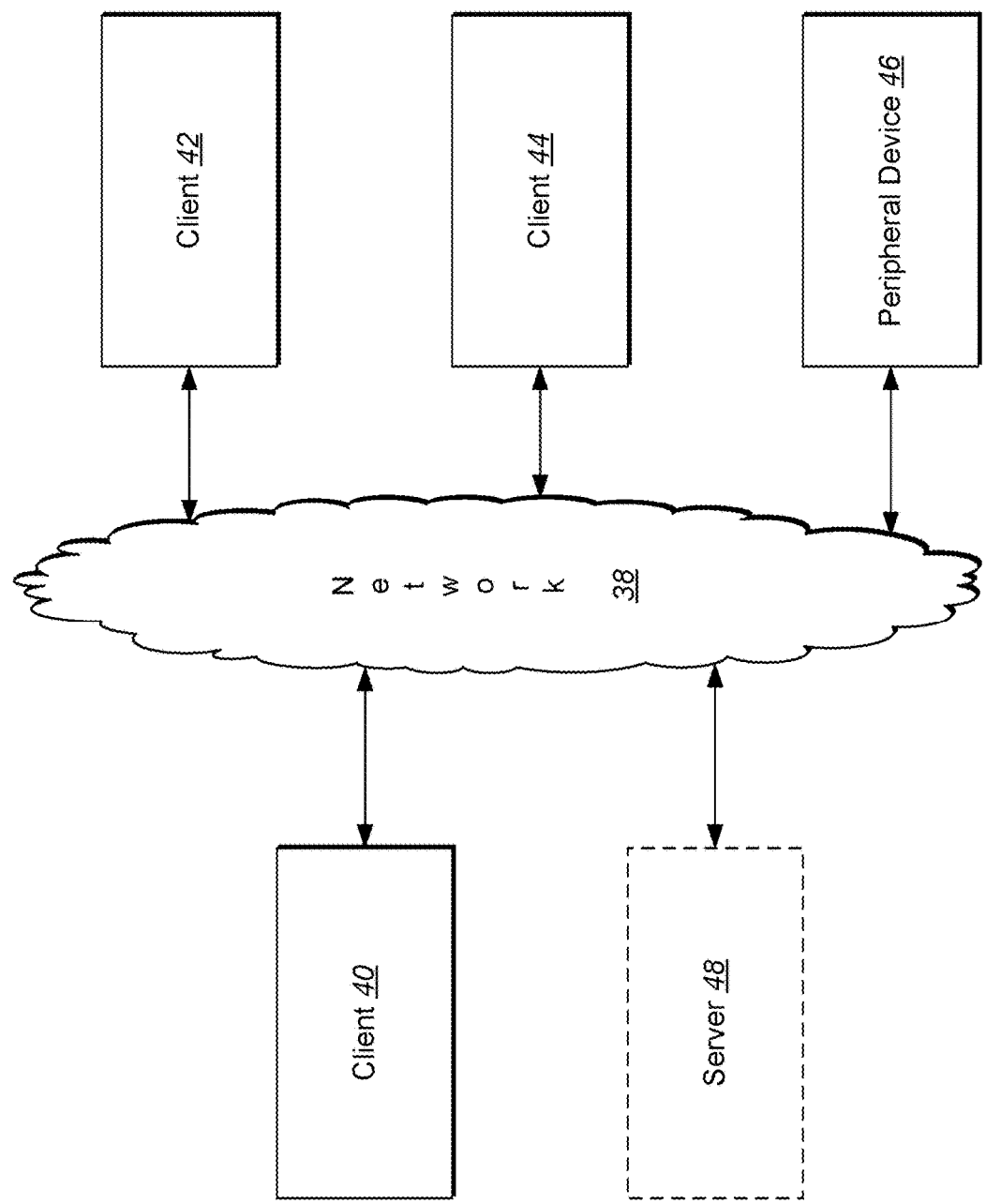
FIG. 2 shows a representative networked system configuration related to embodiments of the present invention.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices (illustrated as multifunctional peripheral (MFP) MFP 46) across network 38. While FIG. 2 illustrates an embodiment that includes a client 40, two additional clients, client 42 and client 44, one peripheral device, MFP 46, and optionally a server 48, connected to network 38, alternative embodiments include more or fewer clients, more than one peripheral device, no peripheral devices, no server 48, and/or more than one server 48 connected to network 38. Other embodiments of the present invention include local, networked, or peer-to-peer environments where one or more computer devices may be connected to one or more local or remote peripheral devices.

Moreover, embodiments in accordance with the present invention also embrace a single electronic consumer device, wireless networked environments, and/or wide area networked environments, such as the Internet.

Similarly, embodiments of the invention embrace cloud-based architectures where one or more computer functions are performed by remote computer systems and devices at the request of a local computer device. Thus, returning to FIG. 2, the client 40 may be a computer device having a limited set of hardware and/or software resources. Because the client 40 is connected to the network 38, it may be able to access hardware and/or software resources provided across the network 38 by other computer devices and resources, such as client 42, client 44, server 48, or any other resources. The client 40 may access these resources through an access program, such as a web browser, and the results of any computer functions or resources may be delivered through the access program to the user of the client 40. In such configurations, the client 40 may be any type of computer device or electronic device discussed above or known to the world of cloud computing, including traditional desktop and laptop computers, smart phones and other smart devices, tablet computers, or any other device able to provide access to remote computing resources through an access program such as a browser.

Software on users' computing devices or applications that would be downloaded on a computer device or firmware updates on the sensor may be employed embodiments of the invention utilizing existing web browser technology. Many browser programs currently exist or are under development, and it would be impossible to name all such browser programs, but examples of such programs include Microsoft's Internet Explorer, Mozilla Firefox, Google Chrome, Apple Safari, Opera Software's Opera browser, as well as myriad browsers specifically configured for specific devices, such as Internet-connected smart phones and the like. The exact display of each browser can vary from browser to browser and most are moderately to highly configurable so as to vary the exact display, Many currently-available browser programs permit the installation of additional features, such as through what are commonly known as "browser extensions." Browser extensions are becoming more and more common in today's browser programs, and have become one of if not the standard for extending the functionality of the browser programs. For browsers that do not currently support browser extensions, other mechanisms and installed programs are often available to provide similar functionality, such as an application downloaded on the computing device.

Embodiments of the invention may utilize a browser extension or similar format to provide functions in accordance with embodiments of the invention. The use and installation of a browser extension is typically significantly less involved and less computer-intensive than the use and installation of a stand-alone program. In many instances, the installation of the browser extension occurs essentially without the computer's operating system being made aware of any additional installation. Instead, the browser program itself handles the browser extension and any demands made by the browser extension.

Embodiments of the present invention may comprise sensors and/or emitters for measuring physical, psychological and physio-psychological characteristics of users and other parameters.

Some embodiments of the present invention may comprise a heart rate monitor. A heart rate monitor may comprise sensors for measuring heart activity. In some embodiments, the electrical activity of the heart is sensed by sensors in the heart rate monitor to measure heart beats. This heart beat data may be measured at the sensor and sent wirelessly to a receiver on another device. Heart rate monitors of embodiments of the present invention may be contained within a wearable device similarly to the accelerometer sensors described above.

Some embodiments of the present invention may comprise a photoplethysmographic (PPG) sensor, which measures blood volume changes in microvascular tissue. A PPG sensor or pulse oximeter may comprise light emitters, such as light emitting diodes (LEDs) that may emit light in multiple frequencies (typically, red and infrared) and measure the difference in the intensity of light received on the other side of the vascular tissue. During a cardiac cycle the blood pressure increases and decreases with the pumping of the heart, these pressure changes expand and contract the arteries causing volumetric changes in the vascular tissue and corresponding changes in tissue volume and absorbed light. The difference in light transmitted through the tissue during a cardiac cycle determines the heart beat profile or PPG profile. Some wearable devices of the present invention may comprise a PPG sensor otherwise known as a pulse oximeter or photoplethysmograph.

The PPG signal may also be used to measure or estimate other physiological parameters. In some embodiments, respiration rate, respiration volume, intrapleural pressure, sinus arrhythmia and other parameters can be calculated from PPG measurements. In some embodiments, the depth of anesthesia and hypo- or hyper-volemic conditions can be measured based on the PPG signal.

Some embodiments of the present invention may comprise a blood glucose sensor for determining the blood glucose level of a user. This sensor may comprise a light-based sensor, similar to the PPG sensor, but measuring blood sugar level, using a light emitter and sensor. Some embodiments may comprise sensors using ultrasound, electromagnetic and thermal sensors to determine blood sugar levels.

Some embodiments of the present invention may comprise sensors that measure a galvanic skin response (GSR) or electro dermal activity. GSR sensors may measure a galvanic skin resistance as an electrical resistance between two electrodes on the surface of the skin and may measure a galvanic skin potential as a voltage between two electrodes on the surface of the skin without any externally applied current. A GSR value may comprise a combination of a skin resistance value and a skin potential value.

Some embodiments utilize a specialized camera such as an otoscope or funduscope as well as sensors that measure external factors such as body temperature, etc.

Figure 3:
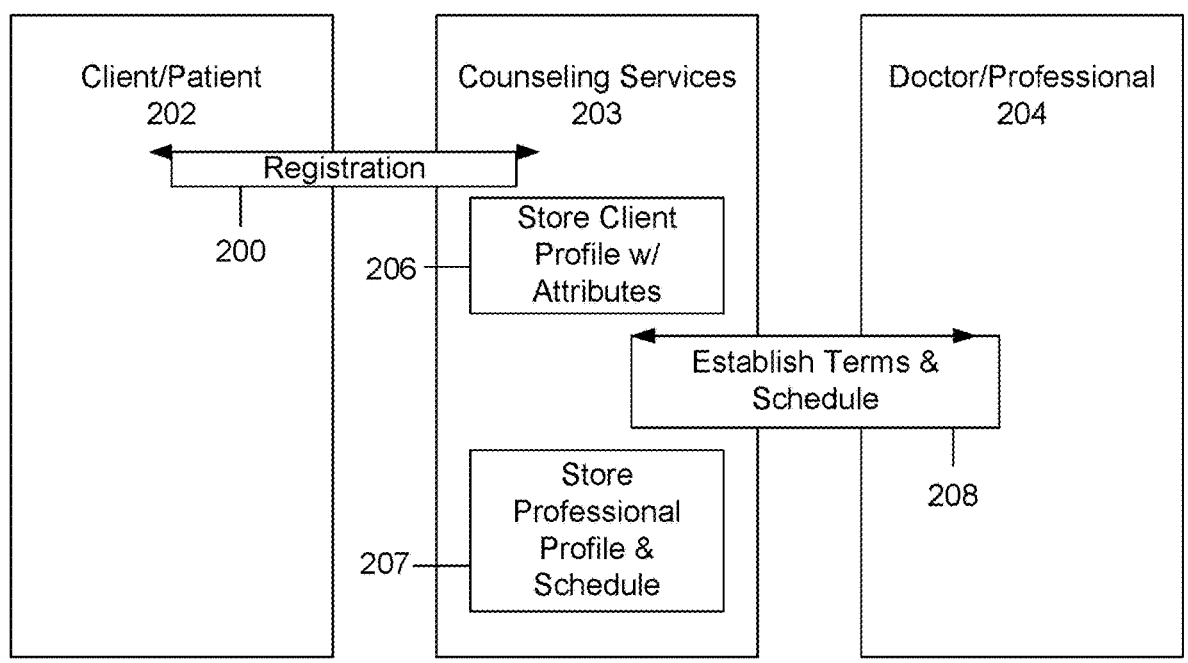
FIG. 3 shows an exemplary embodiment comprising client and professional/expert profile creation.

With reference now to FIG. 3, the invention relates generally to methods and systems for conducting counseling sessions. More particularly, the invention relates to methods and systems for counseling sessions and clinics conducted remotely, such as over the Internet and/or via satellite using WIFI, cellular, microwave, as well as other web-based technologies. In addition, the invention relates to methods and systems for conducting remote counseling sessions by means of various mobile devices as well as biofeedback and/or biometric devices configured to interface with an associated network and/or portal to enhance the efficacy and value of the remote counseling sessions.

Accordingly, methods and systems for online counseling sessions conducted over the Internet are disclosed. In some embodiments, a method for remotely conducting counseling sessions between a client and an expert using an IP-based network includes providing a website accessible to the network wherein the expert and a client both have access to the website. In such embodiments, upon accessing and logging into the website, the client is permitted to search a database for online experts and select an appropriate expert for a counseling session. In some embodiments, the client initially completes various intake and/or registration forms in a virtual waiting room, wherein such forms are customized per the relevant expert. In some embodiments, the user is simply assigned a provider. The method continues as an expert remotely conducts a counseling session with the client via remote means, including video conferencing. Following the counseling session, the client is automatically returned to the virtual waiting room and provided with subsequent counseling based options.

In some embodiments, the methods of the present invention are directed to expert marketing capabilities and/or strategies. In other embodiments, the methods of the present invention are directed to client scheduling or calendaring for counseling sessions, including synchronization with Outlook™, Gmail™, iCal™ or other electronic and/or web-based calendaring systems or programs. In still other embodiments, email, text, SMS messaging, instant messaging and the like are employed to confirm appointments and/or provide reminders of upcoming appointments, to customize general information presented to individual clients, to secure client access to personalized reports and documentation generated by the expert which, in some embodiments, are accessible to individual client and expert only, to provide access to products for purchase selected by the expert for the client, to provide a full accounting and payment system for experts as well as clients, to facilitate client rating and feedback on the expert relative to services rendered or previously provided, and many other aspects as further disclosed herein.

In some embodiments, the network and associated portal employed or used to practice various embodiments of the invention may further be utilized to provide training or educational services for experts categorized by field, topic, and/or experience level. Accordingly, in various embodiments, the methods and systems of the present invention provide resources for both clients seeking counseling as well as experts seeking additional education or training. In all such embodiments, various forms of electronic communication can be used to supplement online counseling sessions and/or training/education such as on demand products, live webcast products, electronic documents or print products and so forth. Experts seeking to use the systems and methods of the present invention can search for and find additional training and/or educational serves from other experts available through the service in much the same way that clients seeking counseling can find specific experts in a relevant field.

Some embodiments enable clients to access counseling services when and where it is most convenient for them, and increase the flexibility of counseling by offering 24-hour availability for pay-per-minute or other pay-per-view sessions. Some embodiments allow experts in any stage of their practice to provide more support to existing clients and to procure new clients regardless of geographical limitations.

In some embodiments, when scheduling an appointment, a client logs in to the expert's website or other type of Internet portal and accesses a scheduling calendar which displays the available counseling sessions. According to some embodiments, the expert has the ability to alter the calendar so that the view is client-dependent. By way of example, in some embodiments the calendar may be manipulated so that fewer "available" counseling sessions are displayed for these clients. In some embodiments, one or more discrete or otherwise independent clinics can also employ the teachings or expert to expert consults disclosed herein to interface and/or coordinate with one another to simplify inter-office scheduling as well as streamlining other document and/or record keeping as well as a host of services that can be offered to a range of clients. In some embodiments, if an expert finds himself or herself without any clients, e.g., due to cancellations, the inability of clients to travel to the office due to severe weather, etc., that expert can toggle an "available" icon on the homepage so that clients desiring counseling know that they can have immediate access without consulting the calendar.

In some embodiments, group counseling sessions can be given. In some embodiments, all clients can see the expert and the expert can see all of the clients at the same time on smaller images on one screen. In such embodiments, the expert can assess the demeanor of the clients as they interact. In some embodiments, the clients will be able to see each other and/or hear each other. In some embodiments, online group counseling can be augmented by occasional private conversations. In some further embodiments, the client or the expert may press a button sending an indication that they desire a private conversation, the expert may then excuse himself or herself from the group discussion and engage in a private conversation shielded from the view and hearing of the other group members. In some embodiments, a hold type button (or a type of privacy button) is provided which allows the expert to pause or temporarily suspend a particular session or to otherwise provide the expert with an opportunity to put the session on hold without actually ending the session. In this way, the expert has the ability to interrupt the session with respect to him or herself without affecting the session relative to other uses in order to protect the client's privacy. Specifically, the expert has the ability to pause the session on his or her end so that if something in his or her environment changes, the expert can control broadcasting such changes to either the expert and/or the other members of the group, or rather has control in order to avoid such a broadcast.

In various embodiments, a "take the floor" feature is offered during a group counseling session. In some embodiments, an expert offers a client the opportunity to lead the discussion by illuminating an icon or reference on the screen in the appropriate location. In some embodiments an "emergency" feature is offered to clients who need emergency contact information for an expert and/or an immediate counseling session with an expert.

In some embodiments, an expert or administrator can designate an assistant who has access to the systems of the present invention, including the portal. In some embodiments, for example, an assistant may be a registered nurse or an expert assistant. In such embodiments, the assistant is capable of meeting with and/or pre-screening clients. Such embodiments further contemplate one or more, including multiple, assistants, some of whom work out of different clinics, working with any number of clients for, in connection with or on behalf of a single practitioner. In this way, one practitioner can be affiliated with multiple clinics and provide counseling or other treatment to multiple clients efficiently and effectively. In some embodiments, multiple assistants associated with multiple clinics are associated with multiple practitioners. In such embodiments, the assistants may have limited access to client information to preserve various privacy aspects and in some embodiments the assistants must be licensed in order to provide assistance.

In some embodiments, an online counseling system is provided according to some embodiments from which experts manage their practice, business, clientele, etc., and/or provide counseling to clients. Consistent with such embodiments, such experts or practitioners have online access to the records of their clientele.

In some embodiments, an expert may utilize a rules engine that automatically assigns a client to an expert.

In various embodiments, experts use the online counseling system as a means of managing their practice, business, clientele, etc. In some embodiments, experts have the capacity to set the rates they charge for their services. In various embodiments, experts may use the online counseling system to record and/or post a brief video introduction detailing their philosophy and credentials for potential clients to review. In some embodiments, experts can manage their schedules from within the system. In various embodiments, secure billing is a feature of the online counseling system. In some embodiments, experts can easily change their billing rate and create and/or edit a customized web page from the system's control center feature. In some embodiments, the online counseling system provides a number of templates from which experts can select to develop a personalized marketing web page displayed from within the online counseling system.

In some embodiments, practitioners create customized virtual waiting rooms for clients. In some embodiments, experts incorporate multiple waiting rooms for use with specific issues, needs, wants, disorders, etc., as a feature of the system. In some embodiments, the system provides experts with an option to create individual templates for particular clients. In some embodiments, after a session, clients may return to a checkout page where they can purchase products chosen by the expert to appear in their online store. In various embodiments, clients have the ability to prepay for a session, or be billed on a per-minute basis, depending on their particular priority or issue. Experts can also decide to not charge for a session. This feature is able to be set manually or through a rule engine. In some embodiments, experts receive receipts on a regular basis for all transactions, which may include items such as monies received, services billed, fees charged and/or collected, etc. In some embodiments, experts have access to current accounting information, data regarding completed and upcoming sessions, client information, and session notes, laboratory information, medical background, legal history, as well as biometric and/or biofeedback information configured to interface with an associated network, mobile apps and/or portal to enhance the efficacy and value of the remote counseling sessions as well as to authenticate the identity of a given client.

In some embodiments, experts may schedule and/or change client appointments and view their schedule via a calendar interface or other easy-to-use interface. In some embodiments, experts may synchronize their online counseling system calendars with Outlook™, Gmail™, iCal™ and/or other suitable calendaring programs. In further embodiments, experts may also synchronize their online calendars with various mobile or handheld devices, other suitable calendar platforms, and the like. In some embodiments, when a client requests a particular time for a counseling session, the system automatically sends that information to the expert, who may either confirm, deny or request to schedule the appointment at an alternative time. If confirmed, in some embodiments, the appointment is automatically added to the expert's calendar. According to some embodiments, experts can set reminders for upcoming appointments via email, short message service (SMS) (i.e. text message), other alerts, etc. In various embodiments, if a client does not cancel a scheduled appointment within a pre-set time frame, experts have the option to indicate their availability for per-minute counseling.

Clients using some embodiments of the present invention have access to a number of services and resources, including any combination of: face-to-face meetings, video conferencing, phone sessions, one-on-one email/text chat, avatar chat, group therapy, message board/email/chat, online support groups, self-help tools, assessment instruments, blogs, SMS, social networking sites, personal websites/online journals, audio and/or video recordings, relaxation and meditation programs, biofeedback, biometric devices, testing devices or programs, and/or other communication or counseling technologies.

In some embodiments, the online counseling system is available up to 24 hours a day. In some embodiments, the online counseling system is configured for use with selected experts (including international experts) to ensure 24-hour consultation availability for clients. In other embodiments, licensed assistants may be employed to facilitate 24-hour availability for clients with respect to certain services for which the assistant is qualified.

In some embodiments, experts may choose, or be required, to enter their qualifications, credentials, etc., in order to register for and/or use or otherwise provide services through the online counseling system. In some embodiments, the qualifications, credentials, insurance, degree, work history, licensing information, etc. that is entered by experts may be individually verified through appropriate channels and/or third party sources. For example, in some instances a medical doctor may register with the online counseling system. Thereafter, his or her license to practice medicine may be verified with state health department(s) or other relevant organization(s) to ensure he or she has not been suspended or that his or her license is not otherwise fraudulent or subject to limitations. In various embodiments, an expert is required to maintain licensure requirements, purchase liability insurance, sign indemnity contracts, etc., before using the online counseling system. For example, in some instances a psychotherapist is required to maintain a license in good standing in order to continue to provide counseling via some embodiments of the present invention. In various embodiments, the online counseling system will offer secure, encrypted methods by which the expert and/or the client may enter his or her personal information.

In some embodiments, clients can grade, rate, provide feedback, score, etc., the services they received. For example, in some instances a user is allowed to submit a rating score after they have spent a predetermined amount of time, e.g., at least 5 minutes, 10 minutes, 20 minutes, 30 minutes, 40 minutes, 50 minutes or an hour with an expert. In some embodiments, a certain number of counseling sessions are required before a client is permitted to rate or otherwise score and expert. In some embodiments, clients can search for experts based on their ranking, location, areas of practice, credentials, years of experience, education, and/or other variables.

According to other embodiments, clients can purchase annual memberships allowing them to use features not available to all base-level users. In various embodiments, clients pay to use the online counseling system. For example, in some embodiments, clients pay an annual membership fee. In other embodiments, however, only third party payers who license the portal pay a licensing fee. In some embodiments, the portal will be given to an expert or other general practitioners free of charge. In some embodiments, experts or their respective organizations may purchase a monthly licensing fee or purchase a block of session call time which may have an expiration date if not used. However, in embodiments contemplating additional training or education for experts or other practitioners, experts seeking additional training and/or education may be required to pay fees in connection therewith according to some embodiments. In other embodiments, additional training and/or educational services are provided free of charge to encourage or entice experts to participate further in the system.

In some embodiments, clients pay a fee to the practitioner as well as a fee associated with using the online services of the present invention. In some embodiments, clients pay a percentage of the expert's counseling session fees in order to use the online counseling system. For example, in some embodiments, clients pay 5%, 10%, 15%, 20% or anything between 1% and 20% on top of what the expert charges in order to use the online services of the present invention. For purposes of illustration, and not by way of limitation, if an expert charges a client session, then the client is required to pay $40 to the expert and 10% of the expert's fee to the online service. As such, in the foregoing example, the client's total bill is $44. In other embodiments, the percentage collected by the online service may be more or less than 10%. In some embodiments, clients are given a discount or other incentives to begin using the online services.

In other environments, a database may be queried to verify an insurance carrier or deductible amount or co-payment that need not be paid by the client. This process will then convey to the client what they need to pay in order to proceed. In this scenario, the above mentioned percentage added on top of the provider fee does not apply.

In various embodiments, advertisers, product manufacturers, private companies, insurance companies, government agencies, or other entities pay money to support the online counseling system, and services are provided to experts and/or users for free or for a reduced price. In various embodiments, experts, clients, and/or other entities can pay for various features, modules, levels, aspects, services, functionalities, etc., of the online counseling system. For example, in some embodiments an expert pays for a monthly fee for a base-level package providing access to most features provided by the online counseling session, and also pays a one-time fee for a pre-designed virtual waiting room for his or her clients. In some embodiments, general practitioners pay a onetime fee. In other embodiments, however, there is no monthly fee for an expert or other general practitioners. Likewise, in other embodiments, there is no onetime fee for experts or other general practitioners. In some embodiments, moreover, third party payers who license the portal pay a licensing fee and provide hosting and/or support for experts and/or practitioners.

In various embodiments, the online counseling system uses secure, encrypted, or otherwise protected methods to exchange data. In various embodiments, the online counseling system includes an on-call system administrator, customer service representatives, or other persons tasked to assist with technical questions and/or handle client or expert inquiries.

In various embodiments, experts have the option to sell any item(s) that they feel might be useful for their client(s). In some embodiments, administrators of the online counseling system collect a percentage, e.g., 5%, 10%, 15%, 20%, 25% 30% or anything between 0% and 30% of the cost of any, or select, products sold by experts through the online counseling system or is charged at the end of the session for items such as lab work or medication. In some embodiments, experts can determine the shipping and handling costs they wish to charge for items sold to clients within the online counseling system. In some embodiments, sales processing is handled by various service providers, e.g., Google Checkout, PayPal, and other suitable service providers common to those of skill in the art.

In some embodiments, experts can set their own billing rates. For example, in some embodiments the expert chooses to either bill a set amount for prescheduled sessions, and to bill clients on a pay-per-minute (PPM) basis for immediate or emergency services. In various embodiments, online counseling system administrators can set the fees or rates charged to use the service. For example, as mentioned above, in some embodiments, clients pay 5%, 10%, 15%, 20% or anything between 1% and 20% on top of what the expert charges in order to use the online services of the present invention. In other embodiments, the percentage collected by the online service may be more or less than 20%. In various embodiments, experts are responsible for their own taxes. In various embodiments, online counseling system administrators charge a fee for tax withholding and other services. In such embodiments, provisions of tax withholding and other services are explained in a terms and conditions document provided to experts during registration with the online counseling system. In some embodiments, experts may be employees and in other embodiments, they may be independent contractors. In other embodiments, the expert is licensing the technology.

In some embodiments, the online counseling system sends the fees for completed sessions to experts on a daily, weekly, bi-monthly, monthly, semi-annually and/or annual basis via wire transfer, less the amount collected in connection with use of the online services, i.e. the percentage on top of what the expert charges for use of the online services, such as 5%, 10%, 15%, 20% or anything between 1% and 20% as discussed previously. In some embodiments, additional fees collected for services and product sales are also sent to experts on a daily, weekly, bi-monthly, monthly, semi-annually and/or annual basis less the cost of any higher-level services for which experts may opt or any additional percentages which are owed to the online service. In some embodiments, practitioners can change their options at any time. When such options are changed, in some embodiments, the billing is prorated when settings are changed in the middle of a billing cycle. In some embodiments, experts can view their account for the past year of services at any time and/or download digital invoices.

In some embodiments, practitioners can designate in advance the times that they are available for prescheduled sessions. In various embodiments, practitioners can designate their availability for on demand or per-minute services. In some embodiments, experts can access a calendar maintained on their computer allowing them to enter prescheduled appointments or designate their on demand or per-minute availability. In various embodiments, the expert's calendar can be synced with their profile to indicate available remaining slots. In some embodiments, experts can choose the view that the public sees of their calendar. For example, in some embodiments the expert chooses to show only currently available slots. In some embodiments, clients can submit a request to a particular expert for a specified time slot. In such embodiments, the request is automatically forwarded to the desired expert or to an assistant designated to assist the expert with respect to the individual client or a group of clients wherein the assistant can confirm or deny the appointment. In some embodiments, if a request for an appointment is confirmed, it automatically schedules a counseling session on the expert's calendar and/or creates automated reminders for the parties involved. In some embodiments, any party can change the frequency of reminders they receive for a particular appointment and/or for all appointments. In some embodiments, if the expert denies a request for an appointment, the client is notified and is given the opportunity to request a different proposed time for a counseling session.

In some embodiments, experts can conduct individual sessions via web cam and/or act as a moderator for group sessions. In various embodiments, groups counseling sessions can consist of one, two, three, four, five, six, seven, eight, nine, ten, eleven, twelve, thirteen, fourteen, fifteen, sixteen, seventeen, eighteen, nineteen, twenty, or more clients. It is contemplated that group sessions can consist of as many clients as the technology used by the online counseling system allows. In some embodiments, the online counseling system incorporates functionality that allows experts to have digital zoom, enhancement, volume, analysis, or other features or capabilities that assist in evaluating clients' body language and/or state of mind.

However, as mentioned above, in some embodiments, a hold type button (or a type of privacy button) is provided which allows the client, expert or expert's staff to pause or temporarily suspend a particular session or to otherwise provide the client, expert or expert's staff with an opportunity to put the session on hold without actually ending the session. In this way, the client, expert or expert's staff has the ability to interrupt the session with respect to him or herself without affecting the session relative to other uses in order to protect the client's privacy. Specifically, the client has the ability to pause the session on his or her end so that if something in his or her environment changes, the client can control broadcasting such changes to either the expert and/or the other members of the group, or rather has control in order to avoid such a broadcast.

In some embodiments, any client and/or expert can record any portion of group counseling sessions (with the exception of control afforded to individual client or expert participants in connection with the privacy button discussed previously). In various embodiments, recordings are downloaded directly to the recording party's computer, and/or are stored remotely on the online counseling sessions' hardware, and/or are stored on a third-party's hardware. In some embodiments, as discussed with reference to FIGS. 1 and 2, cloud-based architectures are contemplated. In such embodiments, recordings or other data stored in connection with any given counseling session may also, or alternatively be stored on the cloud. In some embodiments, storage is held on the cloud be default. In some embodiments, group counseling sessions involving multiple individuals in separate locations are not recordable by client(s) and/or expert(s). In some embodiments, group counseling sessions are recordable only by expert(s).

In various embodiments, calendaring tools are used to facilitate scheduling counseling sessions. In various embodiments, buttons and/or other interface objects providing calendaring options are presented to the client and/or the expert that assist them in scheduling counseling sessions. In some embodiments, experts are given access to a "View Affected" button, a "View Conditions" button, a "Restrictions" button, or something similarly entitled, which permits an expert to view and/or place restrictions on clients' ability to view and/or schedule appointments, availability for appointments and/or private time. In some embodiments, access is given to experts through the use of such buttons, or similarly titled buttons, which permit the expert to modify or otherwise alter certain components of client information, including in some embodiments personal information, as well. For example, in some embodiments an expert can limit the client to one session per day, per week, etc., so as to prevent a client from needlessly over-scheduling counseling sessions. In some embodiments, the expert can restrict a client from viewing and/or scheduling counseling sessions during specific times or dates. For example, in some embodiments a client who has insurance that pays a set fee or a low fee can be restricted to view and/or schedule only off-peak hours or dates.

In other embodiments, when an expert is unable to be on-time for a counseling session, the expert can press the "View Affected" button, or something similarly titled, permitting the expert to see which counseling sessions are affected and providing options regarding what can be done to reschedule the affected counseling sessions, or click on the name of the person in the waiting room and redirect them to another expert either automatically or manually. This can be done by the expert or expert's staff. In various embodiments, clients are given access to an "Emergency" button, a "Get Help Now" button, a "Hotline" button, or something similarly entitled, which permits a client to receive counseling immediately. An expert may also click on the name of the person in the waiting room and redirect them to another expert either automatically or manually. This can be done by the expert or expert's staff. In some embodiments, pressing the "Emergency" button, or similarly entitled button, sends an alert to available experts. In such embodiments, an expert may confirm the alert and begin a counseling session with the client who indicated they were in emergent need. In various embodiments, clients are given access to a "See Immediate" button, a "See Available" button, or something similarly entitled, which allows clients to view and/or schedule counseling sessions with experts who are currently available, regardless of whether or not there is emergent need.

In various embodiments, dynamic tools are used to improve counseling sessions. In various embodiments, buttons and/or other interface objects providing dynamic abilities to mute, start, stop, enhance, emphasize, record, remove, re-organize, delay, pause, forward, rewind, and/or other dynamic abilities, are presented to the client and/or the expert that improve the ability to provide care during the counseling sessions. For example, in some embodiments the expert uses a "Privacy" button, a "Go Private" button, or other something similarly entitled, to speak, text, or otherwise communicate in private with a subset of clients during a group counseling session. In some embodiments, the effect would be to reduce or mute the audio, text, video capabilities, and/or restrict other forms of communication for the group member(s) who were not invited to speak in private. In other embodiments, similarly entitled buttons are available to a client to temporarily pause a given counseling session so as to preserve his or her privacy if the environment he or she is in during the session changes and the client prefers not to broadcast his or her environment for a period of time without ending the session altogether. In such embodiments, the remaining members of the session (i.e. experts and/or other clients) are permitted to continue with the session in progress. In some embodiments, the use of a dynamic tool has the effect of reducing or muting what the clients can type, hear, see, and/or restrict other forms of communication. In some embodiments, the use of a dynamic tool has the effect of playing a predetermined text, audio track, video clip, and/or other communicative presentation.

In some embodiments, the expert and/or client has access to a "Take the Floor" button, an "I Hold the Conch" button, or something similarly entitled, that allows only a subset of clients to "take the floor," i.e., speak, type, or otherwise communicate during a group counseling session without allowing others to speak, type, or otherwise communicate. In some embodiments, only the expert has the power to grant the ability to take the floor. In some embodiments, the client has to request permission from the expert and/or group before being able to take the floor. In some embodiments, the client is allowed to take the floor only for a set amount of time; in other embodiments, the client may receive the right to take the floor for the full length of the counseling session. In some embodiments, the person(s) who have taken the floor are emphasized by some text, audio, or visual indication. For example, in some embodiments a group counseling session that has both audio and video feeds in which taking the floor has the effect of increasing that client's volume and chat window size, while reducing the other clients' volume and chat window size. In some embodiments, for example, a digital zoom function is provided to facilitate the emphasis of the individual taking the floor. The expert may take back control at any time.

In some embodiments, when a client requests a specific expert for a pay-per-minute session, and the expert does not connect with the client for a session within a set time period, the client has the option to send an email requesting that the expert provide information about their next available time slot. In some embodiments, clients can be redirected to a page listing alternative experts currently online that meet the client's desired criteria. Clients may also request an appointment that does not have a specified end time. Experts can also send out an appointment request or invitation to a session that does not have a specified length of session time.

In some embodiments, an online counseling system allows experts to design or import documents they deem necessary for services provided to their clients. In some embodiments, files created by experts for a particular client can be downloaded to the expert's computer and/or the client's computer. In alternative embodiments, such files and/or documents are made available in real time via cloud architecture as discussed with reference to FIGS. 1 and 2. In various embodiments, the online counseling system enables experts to integrate various client records with information from other sources. For example, in some embodiments, records generated during online counseling sessions can be integrated with records obtained from a third-party. In various embodiments, the process of generating records or other files and/or documents during an online counseling session are created via an application integration utility (AIU), API, ISON database connection/callback or other interface.

In various embodiments, the online counseling system is used for more than individualized and/or group counseling sessions, but is also used for training programs and educational sessions. For example, in some embodiments an online counseling system is used to teach mental health classes, pre-nuptial classes, birthing classes, shaken-baby training, anger-control training, language training, diabetes education, cooking, exercise or physical therapy, etc. In other embodiments, various educational and/or training programs are provided with respect to specific fields of study in which students are provided with supervised opportunities to practice or apply certain teachings commensurate with learning such information or shortly thereafter. In other words, some embodiments contemplate the provision of hands-on experience with certain educational features or subjects or otherwise contemplate the provision of a practicum which enables students to apply theoretical knowledge contemporaneously with the acquisition of such knowledge.

In various embodiments, the online counseling system is used by experts fluent in various different languages. For example, in some embodiments refugees are taught English classes by an expert who speaks their native language which facilitates the language instruction. In another non-limiting example, in some embodiments a deaf individual may receive psychotherapy treatment using a videoconferencing feature of the online counseling system from an expert psychologist who speaks American Sign Language. In such embodiments, such therapy, counseling and/or educational information is provided in the first language of the client in order to maximize the efficacy of such sessions.

In other embodiments, counseling and/or educational sessions are also available via video counseling and associated technologies for incarcerated persons, such as people in jail, prison, mental institutions and other formats where clients are unable or precluded from leaving a given facility but yet have access to Internet or web-based services. In such embodiments, counseling and/or education could be provided as a means of treating incarcerated individuals or other persons with mental or emotional challenges.

Various embodiments that use the online counseling system described herein to provide counseling sessions may be called "TruClinic." For example, in some embodiments psychotherapy services are provided through an online counseling system called TruClinic. Some embodiments include a control center for experts to change any aspect of their marketing information and billing rate. Some embodiments include a billing matrix/payment management system that allows experts to charge whatever they choose, with a preset minimum, such as the non-limiting example in which an expert charges $1.00 per minute with a $25.00 minimum. In other embodiments, there is no minimum charge; rather clients are permitted to access the system and participate in a session on a pay-per-minute basis while being allowed to terminate the session at any time without incurring a minimum charge. In this way, clients are not discouraged from trying the services for fear of incurring a minimum charge.

In some embodiments, the present invention may be white labeled to appear under the brand and style of the expert's website.

Some embodiments include a module that allows experts to record a brief introduction of themselves, as well as an overview of the services they provide. Some embodiments of TruClinic include a digital or virtual waiting room for which experts can set up various wallpapers or backgrounds depending on the client they are seeing. For example, in some embodiments the expert is working with someone that has post-traumatic stress disorder, and can utilize a pre-made or customized virtual waiting room populated with questionnaires, articles, videos, and particular products for sale, such as books about the disorder. In some embodiments, such features may be managed from the expert's control center within the online counseling system.

Some embodiments include regularly and/or immediately updated accounting and statistical information regarding the expert's practice. Some embodiments may include a scheduling and client management system that will remind clients and/or experts of appointments via email, text message, a computer alarm, social networking such as Facebook, Twitter, as well as SMS, instant messaging, etc. In some embodiments experts can synchronize their calendar with various calendar programs as discussed previously.

Some embodiments of the present invention include a module that allows experts to record a session (starting at any point during the session) without maintaining any records of client/expert appointments or interactions. Embodiments of the present invention are fully compliant with all internet protocols, security standards, confidentiality standards, or other requirements imposed on experts of businesses in various fields. For example, in some embodiments some embodiments that provide medical and/or psychotherapeutic counseling services are fully compliant with the confidentiality and record-keeping standards imposed by the Health Insurance Portability and Accountability Act of 1996 ("HIPAA"). In addition, embodiments of the present invention are fully compliant with standards propagated, established, maintained and/or enforced by Health Level Seven International, the American Medical Association, the American Psychological Association, the Telemedicine Association, CTEL and Assessment & Treatment Alternatives clinic among other health or services oriented organizations with regard to the interoperability of health information technology and associated protocols.

Some embodiments include allowing experts from the United States, and/or experts from countries with similar standard-of-care modalities as those in the United States to use the present invention to provide online counseling services. In such embodiments, internationally-based experts are required to meet United States standards related to medical records, information, confidentiality, etc. For example, in some embodiments experts from Great Britain, Germany, New Zealand, Ireland, Scotland, Australia, France, Japan, and Canada are eligible to register and/or use such embodiments because psychotherapy experts in those countries are required to meet standards comparable to those imposed here in the United States. The foregoing list of countries that may be permitted to register and/or use various embodiments is merely illustrative and may be reduced, supplemented, augmented or otherwise modified according to various embodiment of the present invention. Some embodiments conform to international or specific countries by implementing the needed architecture to meet additional rules or regulations.

The embodiments of online counseling systems provided herein provide many advantages. Various embodiments ensure privacy and confidentiality assuring clients they can express themselves freely, which assists in the provision of effective counseling. Various embodiments assist individuals to receive counseling at critical times. Because of their worldwide reach, flexible scheduling, and/or 24-hour availability, various embodiments make effective counseling available at convenient times and places, and/or at a price that is sustainable for many clients. For example, such embodiments can provide important counseling for veterans, military personnel, indigent, home-bound, in jail, or other persons who cannot or are too far away to travel to a traditional brick-and-mortar building to receive counseling, etc. In various embodiments, because the technology is able to simulate real-time, in-person interactions, experts can provide the same kind of services they would be able to provide were they to meet the client in-person, but do so in a manner that allows the client to meet in a space of their choosing that is comfortable for them, making them more likely to be at ease during the therapy session, thus increasing the likelihood of effective communication and effective therapy.

In various embodiments, the use of virtual or "digital" waiting rooms help to put clients at ease and enable the expert to further replicate the experience of in-person interactions. In various embodiments, if a client cancels his or her counseling session, experts can use the flexible scheduling features to recoup time that would have otherwise been lost in a solely brick-and-mortar practice. In various embodiments, the ranking and feedback feature(s) provide clients with the ability to assess and experiment with experts and to locate the expert(s) that perfectly meet their needs on an immediate and/or long-term basis. In other embodiments the client does not have this ability because the platform is only being used by the client's expert and the client may or may not have created an account in the system depending on how the expert decides to use the tools that re available to him.

Some embodiments of the present invention minimize or eliminate much of the overhead associated with running a traditional counseling office, e.g., such as rent, fees, utilities, and staff. Some embodiments of the invention enable experts to provide effective services to clients in any location, thus increasing their potential client base and referral pool to a worldwide scale. Some embodiments of the invention also enable experts to work the hours they prefer, since clients can be in any time zone. Some embodiments of the present invention create new client and service opportunities for experts. Some embodiments of the present invention allow experts who are just starting their businesses to have a viable and economical alternative to the high-cost structure of joining a group of other experts to start building a client base. Some embodiments allow experts with an established practice to expand their reach by offering existing clients the option to use online consultations to supplement regularly scheduled in-person appointments. Some embodiments allow experts looking to scale back their practice for such reasons as imminent retirement to continue to provide high-quality services to select long-standing clients without the expense and stress associated with maintaining a physical office environment. Other counseling models may include concierge, fee for service or direct to consumer counseling models.

In some embodiments of the present invention, entrance codes can be provided to allow clients to enter a waiting room. For example, when scheduling an appointment, a client can be provided an entrance code that will allow him to enter the waiting room at an appropriate time. In some embodiments, the expert or an administrator of the system can deactivate an entrance code to prevent the client from using it to enter the waiting room. Also, in some embodiments, after a client has used an entrance code to enter a waiting room, the expert or other administrator can remove the client from the waiting room without deactivating the entrance code used by the client to enter the waiting room. In this way, the client can reenter the waiting room using the same entrance code at a later time.

In some embodiments of the present invention, anonymous entrance codes can be employed to allow a client to anonymously enter an expert's waiting room to conduct an anonymous counseling session. For example, the expert may email or otherwise transmit anonymous entrance codes to clients.

The present invention can be used by experts to provide counseling sessions in many different medial fields including but not limited to: Addiction Medicine, Adolescent & Young Adult Medicine, Allergy/Immunology, Anatomic Pathology & Laboratory Medicine, Anesthesiology, Blood Banking/Transfusion Medicine, Body Imaging, Cardiology, Chemical Pathology, Child/Adolescent Neurology, Child/Adolescent Psychiatry, Clinical Cardiac Electrophysiology, Critical Care Medicine, Cytopathology, Dermatology, Dermatopathology, Diagnostic Radiology, Diagnostic Roentgenology, Diagnostic Ultrasound, Emergency Medical Services, Emergency Medicine, Facial Plastic Surgery, Family Medicine and OMT, Family Physicians, Female Pelvic Medicine/Reconstructive Surgery, Forensic Pathology, Gastroenterology, General Vascular Surgery, Geriatric Medicine, Geriatric Psychiatry, Gynecologic Oncology, Hand Surgery, Hematology, Hematology-Pathology, Home Health, Hospice, Hospice and Palliative Medicine, Immunopathology, In Vivo and In Vitro Nuclear Medicine, Infectious Disease, Internal Medicine, Interventional Cardiology, Laboratory Medicine, Maternal and Fetal Medicine, Medical Microbiology, Medical Toxicology, MOHS-Micrographic Surgery, Nephrology, Neurological Surgery, Neurology, Neuromusculoskeletal Medicine & OMM, Neuropathology, Neurophysiology, Neuroradiology, Nuclear Cardiology, Nuclear Imaging and Therapy, Nuclear Medicine, Nuclear Radiology, Obstetrics & Gynecology, Obstetrics & Gynecology Surgery, Occupational Medicine, Oncology, Ophthalmology, Orthopedic Surgery, Otolaryngic Allergy, Otolaryngology, Otolaryngology/Facial Plastic Surgery, Pain Management, Pain Medicine, Palliative Medicine, Pediatric Endocrinology, Pediatric Pulmonology, Pediatric Radiology, Pediatrics, Physical Medicine & Rehabilitation, Plastic & Reconstructive Surgery, Preventive Medicine, Preventive Medicine/Aerospace Medicine, Preventive Medicine/Occupational, Preventive Medicine/Occupational-Environmental Medicine, Preventive Medicine/Public Health, Proctology, Psychiatry, Radiation Oncology, Radiation Therapy, Radiology, Reproductive Endocrinology, Rheumatology, Roentgenology, Sleep Medicine, Sports Medicine, Surgical Critical Care, Thoracic Cardiovascular Surgery, Undersea and Hyperbaric Medicine, Urological Surgery, and Vascular & Interventional Radiology.

The present invention can also be used by experts to provide counseling sessions in many different surgical sub-specialties including but not limited to Amputations, Bariatrics, Cardiac Surgery, Endocrine Surgery, Eye Surgery, General Surgery, Gynecological Surgery, Neurosurgery, Oral and maxillofacial surgery, Orthopedic surgery, Otolaryngology, Plastic Surgery, Proctology, Surgical Oncology, Thoracic Surgery, Trauma surgery, Urology, Vascular surgery, Abdominal Surgery, Cardiothoracic surgery, Dental Surgery, Endoscopic Endonasal surgery, Neurointerventional surgery, Orthognathic surgery, Pediatric surgery, Shoulder surgery, and Urogynecology.

The present invention can also be used by experts to provide counseling sessions in many different nursing sub-specialties including but not limited to: Ambulatory care nursing, Advanced practice nursing, Burn nursing, Camp nursing, Cardiac nursing, Cardiac catheter laboratory nursing, Medical case management, Community health nursing, Correctional nursing, Critical care nursing, Emergency and trauma nursing, Environmental health nursing, Faith community nursing, Flight nursing, Forensic nursing, Gastroenterology nursing, Genetics nursing, Geriatric nursing, Health visiting, Holistic nursing, Home health nursing, Hospice and palliative care nursing, Hyperbaric nursing, Immunology and allergy nursing, Intellectual disability nursing, Intravenous therapy nursing, Infection control nursing, Infectious disease nursing, Legal nursing, Learning disability nursing, Maternal-child nursing, Medical-surgical nursing, Mental health or psychiatric nursing, Military and uniformed services nursing, Neonatal nursing, Neurosurgical nursing, Nursing informatics, Nursing management, Nursing research, Nursing midwife, Obstetrical nursing, Occupational health nursing, Oncology nursing, Orthopedic nursing, Ostomy nursing, Pediatric nursing, Perianesthesia nursing, Perioperative nursing, Private duty nursing, Psychiatric or mental health nursing, Public health nursing, Pulmonary nursing, Quality improvement, Radiology nursing, Rehabilitation nursing, Renal nursing, School nursing, Space nursing, Sub-acute nursing, Substance abuse nursing, Surgical nursing, Telenursing, Telephone triage nursing, Transplantation nursing, Travel nursing, Urology nursing, Utilization management, and Wound care.

The present invention can also be used by experts to provide counseling sessions in many different mental health specialties/sub-specialties including but not limited to: Abuse, Academic, Addictions, Adjustment, Adolescents, Adoption, Adults, AIDS/HIV, Alcohol Abuse, Alzheimer's/Dementia, Anxiety/Panic, Attention Deficit Hyperactivity, Autism Spectrum, Behavioral Issues, Behavioral Medicine, Bipolar, Borderline Personality Disorder, Brain Injury (TBI), Business Consultation, Cancer/Terminal Illness, Caregiver Support, Child, Child Abuse, Children of Alcoholics, Children of Mentally Ill, Chronic Pain or Illness, Clinical, Codependency, Compulsive Gambling, Conduct Disorder, Consultation—Liaison, Cultural Issues, Cyberbullying, Deaf/Hard of Hearing Issues, Depression, Developmental Disorders, Diabetic, Disability, Disaster Intervention & Recovery, Dissociative, Divorce/Custody, Domestic Violence, Drug Abuse, Dual Diagnosis, Eating Disorders, Elder Abuse, Elder/Geriatric, Executive/Career/Life Coaching, Family Issues, Forensic, Gender Identity Concerns, Grief, Holistic, Hospital, Impulse Control, Individuals, Infants, Infertility, Integrative Medicine, Internet Addiction, Intimacy Issues, Learning Disabilities, Legal Issues, Life Transitions, Marital Counseling, Mediation/Collaboration, Medication, Mens Issues, Mental Conditions, Mental Deficiency, Military Issues, Mood Disorders, Narcissistic, Neuropsychiatry, Neuropsychology, Obesity, Obsessive Compulsive, Occupational Psychiatry, Oppositional Defiant, Organizational Psychology, Other, Parenting Issues/Training, Personality Disorders, Phobias, Pornography addiction, Post-Traumatic Stress Disorder/PTSD, Postpartum, Psychological Educational Consultations, Psychological Testing, Psychological Trauma, Psychosomatic, Relationship Issues, Reproductive, Schizophrenia/Psychosism, Self-Esteem Issues, Self-Harm/Suicide, Sexual Harassment, Sexual Issues, Sleep/Insomnia, Spiritual Concerns, Sports Psychology, Stalking, Stress Management, Telepsychiatry/Telemedicine, Violent Offenders, Women's Issues, Work Issues, and Workers Compensation.

The present invention may also be used by experts to provide counseling sessions in many different veterinarian fields including but not limited to: Alternative medicine, Anaesthesiology, Animal behavior, Animal welfare, Birds (pet and ornamental), Bovine, Canine, Cardiology, Chiropractic, Clinical pathology, Clinical pharmacology, Dentistry, Dermatology, Diagnostic imaging, Equine, Emergency and critical care, Exotics, Feline, Internal medicine, Laboratory animal medicine, Microbiology, Neurology, Nutrition, Oncology, Ophthalmology, Parasitology, Pathology, Poultry, Preventive medicine, Radiology, Reptile and amphibian, Shelter medicine, State veterinary medicine, Sports medicine, Surgery, Theriogenology, Toxicology, Veterinary Surgery, and Zoo animals and wildlife.

The present invention may also be used by experts to provide counseling sessions in many different legal fields including but not limited to: Administrative law, Admiralty law, Advertising law, Agency law, Alcohol law, Alternative dispute resolution, Animal law, Antitrust law, Appellate practice, Art law, Aviation law, Banking law, Bankruptcy law, Bioethics, Bird law, Business law, Business organizations law, Class action litigation/Mass tort litigation, Communications law, Computer law, Conflict of law (or private international law), Constitutional law, Construction law, Consumer law, Contract law, Copyright law, Corporate law (or company law), Corporate compliance law and corporate governance law, Criminal law, Cryptography law, Cultural property law, Custom law, Cyber law, Defamation, Derivatives and futures law, Drug control law, Elder law, Employee benefits law (ERISA), Employment law, Energy law, Entertainment law, Environmental law, Equipment finance law, Evidence, Family law, FDA law, Financial services regulation law, Firearm law, Food law, Franchise law, Gaming law, Health law, Health and safety law, Health care law, Immigration law, Insurance law, Intellectual property law, International law, International trade and finance law, Internet law, Labor law, Land use & zoning law, Litigation, Martial law, Media law, Mergers and acquisitions law, Military law, Mining law, Juvenile law, Music law, Mutual funds law, Nationality law, Native American law, Obscenity law, Oil & gas law, Parliamentary law, Patent law, Poverty law, Privacy law, Private equity law, Private funds law/Hedge funds law, Procedural law, Product liability litigation, Property law, Public health law, Railroad law, Real estate law, Securities law/Capital markets law, Social Security disability law, Space law, Sports law, Statutory law, Tax law, Technology law, Timber law, Tort law, Trademark law, Transport law/Transportation law, Trusts & estates law, Utilities Regulation, Venture capital law, and Water law.

The present invention may also be used by experts to provide counseling sessions in many different dental fields including but not limited to: Dental Public Health, Endodontics, Oral and Maxillofacial Pathology, Oral and Maxillofacial Radiology, Oral and Maxillofacial Surgery, Orthodontics and Dentofacial Orthopedics, Pediatric Dentistry, Periodontics, and Prosthodontics.

The present invention may also be used by experts to provide counseling sessions in many other fields including but not limited to: Art, Music, Computers, Electronics, Cooking, Fashion & Beauty, Fitness, Mechanics, Education, Programming, Nutrition, Home & Garden, and Health & Wellness.

Some embodiments of the present invention may be described with reference to FIG. 3. These embodiments relate to a client or patient registration 200 with an exemplary system. In these embodiments, a client and/or patient 202 may access the system using a computing device such as a home computer, laptop, tablet, cell phone or another computing device with a network interface. Counseling services 203 may be implemented via an internet server or cloud services platform that is connected to the internet or some similar network. In some embodiments, a doctor or some other professional or service provider 204 may also access the system via a home computer, laptop computer, tablet, cell phone or some other computing device. Typically, the client computing device 202 and professional computing device 204 will access the counseling services server 203 using a network connection such as a wireless network connection or wired connection, which may utilize a TCP/IP protocol or some other networking protocol.

In some embodiments, the client/patient computing device 202 and professional computing device 204 may employ a browser to access content served up by the counseling services server 203. In some embodiments, the client device 202 may access the internet or similar network to connect to an initial web page offered up by the counseling services server 203. This initial web page may be accessible by a public facing universal resource locator (URL), which may or may not be password protected. The initial web page may offer registration options 200. These options may comprise an option to register a new un-referred user, an option to register a referred user with a one-time referral code, an option to register a user with a long-term referral code, an option to proceed without registration and/or other options.

An un-referred user may access the site via URL input, via a search portal or by other methods. Once the site is accessed, the un-referred user may register by selecting a registration option and by inputting personal information, counseling needs data, billing information, a username, a password and other information as needed. The counseling server 203 may then filter participating professionals' records and provide access to expert/counselor/doctor/professional data for experts who match the user's counseling needs. The user may then select an expert from the filtered options.

A referred user with a one-time access code may access the initial web page by various methods. This user may then enter the one-time access code as optional input in the initial web page. The one-time access code may have been issued by a specific professional or by a specific group of professionals or by a sponsor for a professional or group thereof. The one-time access code may be associated with one or more professionals and, upon entry, may link the user to those one or more professionals' websites, calendars, scheduling system, availability data, messaging center, document center or another connection. The one-time access code may also be associated with the user's personal information, which may have been input to the system by the entity who issued the code. Accordingly, the referral code may serve to automatically register the user without tedious personal data input and may also serve to automatically link the user with one or more experts.

A referred user with a long-term access code may access the initial web page by various methods. This user may then enter the long-term access code as optional input in the initial web page. The long-term access code may have been issued by a specific professional or by a specific group of professionals or by a sponsor for a professional of group thereof. The long-term access code may be associated with one or more professionals and, upon entry, may link the user to those one or more professionals' waiting room(s), websites, calendars, scheduling system, availability data, messaging center, document center or another connection. A long-term access code may be used multiple times to access the same expert or group of professionals. The long-term access code may also be associated with the user's personal information, which may have been input to the system by the entity who issued the code. Accordingly, the long-term referral code may serve to automatically register the user without tedious personal data input and may also serve to automatically link the user with one or more experts. A long-term referral code may also be associated with a user's billing information, another facility of linked to a non-personal identification number.

In some embodiments, a user may access the initial web page and proceed to some services offered thereon without completing a full registration process. In these embodiments, a partial registration may be completed or the registration process, or a portion thereof, may be delayed until more information about available professionals or services is obtained by a user, client or potential client.

In some embodiments of the present invention, once a user is registered (e.g., their personal and billing data is on file), meaning that the personal and billing data may be hosted and stored by a third party and a token is sent or approval of any charge levied to the end user. In some embodiments, the vendor never sees the account info, just an approval. Sub-accounts may be created under the user's registration. For example, the dependents of a user may create sub-accounts by entering the user's specified personal data to link their sub-account to the user's initial account. Accordingly, the sub-accounts may share authorization data, billing data and other information and permissions while preserving distinct information files such as medical records and appointment schedules for each sub-account.

In some embodiments, once a user has input personal information during a registration process 200 via a web site or another data entry process, the personal information may be stored in a client profile record 206. A client profile record 206, may comprise a user's name, address, phone number, email address, profile picture, social media identifiers, age, sex, marital status, number of children, medical history, family medical history, current medical, psychological or other counseling needs, conditions, billing data, credit card data, bank account data and other information described above and elsewhere.

In some embodiments, experts such as doctors, psychologists, lawyers, counselors, realtors, professionals, service providers and others 204 may also register to provide services to clients 202 through the counseling services platform 203. In some embodiments, the expert 204 may access the same initial web page that a user may use to register or a separate web page interface may be provided for experts 204. In any case, an expert may access an expert registration page that facilitates exchange of information between the expert 204 and the counseling services platform 203. An expert may input personal and business information, credit card data, banking data and other information to facilitate business transactions. An expert may also input 208 service descriptions, payment terms and a calendar or schedule. This information may be stored by the counseling services platform 203 as an expert or professional profile and schedule 210.

This expert profile 210 may be accessed in search operations to find a match between the needs of a user 202 and the services offered by an expert 204. When a match occurs, a user 202 may be connected with an expert 204 through the counseling services platform 203. This can be automatically done via a software algorithm or some other mechanism, or be done manually by a customer/company's assigned representative.

Figure 4:
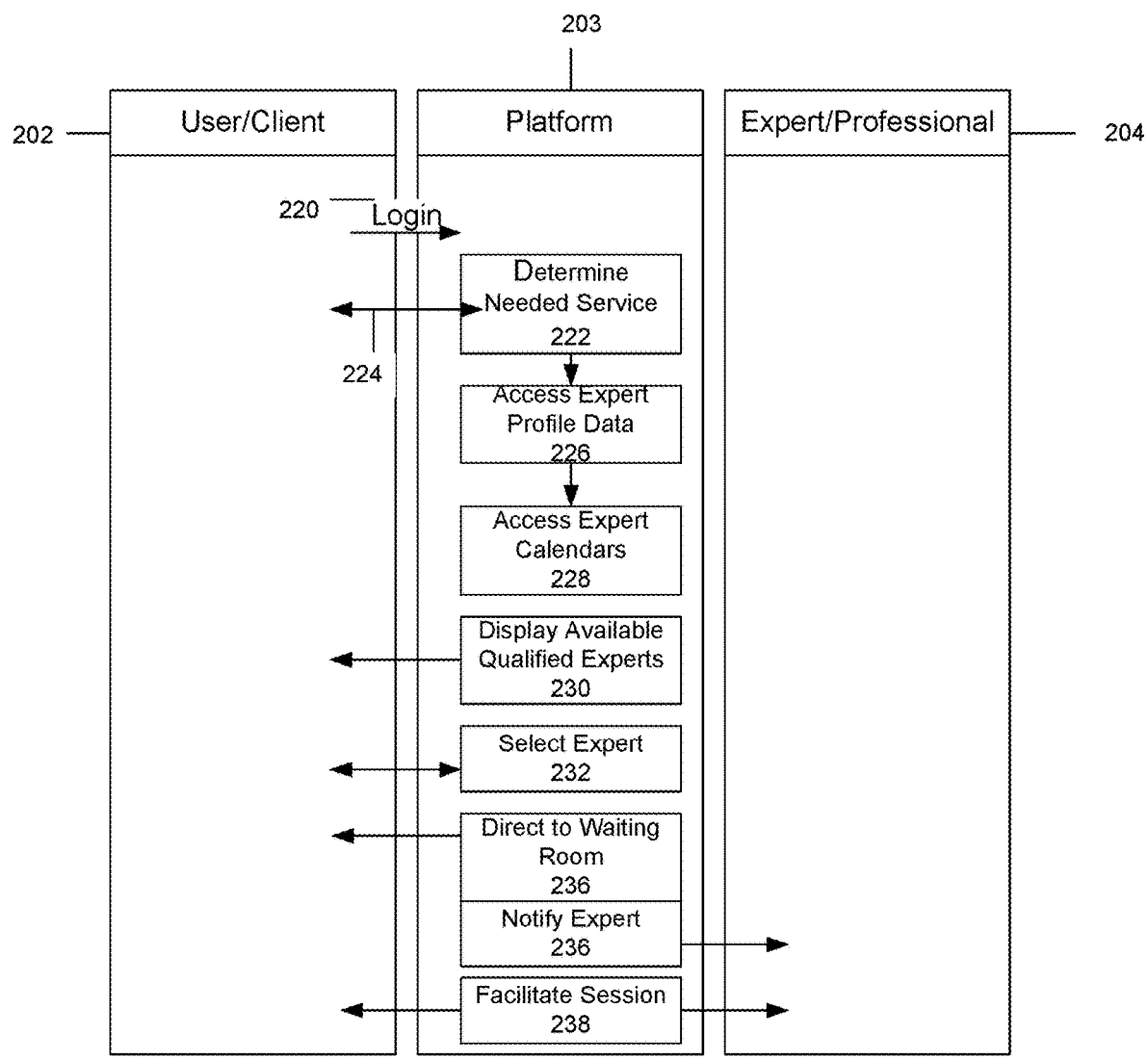
FIG. 4 shows an exemplary embodiment comprising an expert search.

In some embodiments of the present invention, illustrated in FIG. 4, a user 202 may log in 220 to the platform 203 through typical methods using a username and password or by other methods. When the user 202 logs in, the platform 203 may access the user's profile 206 to determine the user's known service needs 222. Additionally, the user 202 may be presented with a web page that provides for input 224 relative to the user's currently-desired services.

In some embodiments, the platform 203 may comprise a Role and Permission based system with different functionality sets, wherein different user types have access to different feature sets. In some embodiments, data in the user's profile 206 may be accessed and may be supplemented with current input to determine services that are likely to be desired by the user. The expert profiles 210 may then be searched 226 to determine whether any experts 204 are qualified and available to provide those services. In some embodiments, expert calendars 228 may be accessed to determine availability. In some embodiments, an expert may log in and indicate current availability status, or hide their profile so they are not searchable, except by internal staff.

If one or more matches are found, the list of available, qualified experts 204 may be displayed 230 to the user. For example, if a user's profile indicates that depression counseling is desired, the platform 203 may link the user to a set of counselors or psychologists who provide that service and whose status is currently available. This can be done automatically or manually. As another example, a user whose profile indicates a need for a real estate transaction may be linked to a set of professionals who can accomplish that task and whose status is currently available.

In some embodiments, after log-in has occurred, a user 202 may be automatically or manually directed to a specific service provider 204 based on perceived user needs indicated in the user profile 206. In some cases a group of service providers may be filtered to determine which providers are immediately available and this filtered list may be offered to the user automatically upon log-in. In some cases, a provider 204 with the shortest waiting time may be referred when none are immediately available. In some cases, a user 202 may have a preferred service provider who will be connected with the user 202 upon log-in, however, another expert 204 may be referred if the preferred expert is not available.

When the user 202 is presented with a plurality of available experts 230, the user may review the expert profile data of each expert and make a selection 232. In some embodiments, the user 202 may then be directed 234 to a virtual waiting room associated with the selected expert. The selected expert may also be notified 236 of the user's selection and their status in the waiting room. The virtual waiting room may comprise a web page with links to online chat with an expert or an associate, documents maintained by the associated expert, email to the associated expert, facilities related to the associated expert's services and other links and data. When both the expert 204 and the user 202 have indicated readiness, an online session 238 between the user 202 and the expert 204 may be facilitated by the platform 203. This online session 238 may comprise a videoconference, an audio conference, a chat forum, virtual messaging, document exchange and other media functions.

In some embodiments, a user 202 may be automatically or manually redirected to an alternate expert when the selected expert becomes unavailable or is found to be unable to resolve the user's issue. In some embodiments, a first expert may generate a referral for a user/client 202 to visit a referred expert when a need or desire for another expert is discovered. In these embodiments, the referral may comprise data identifying the first expert and the referred expert as well as the client/user. The referral process may automatically transfer a user's files, documents, history and/or other data to the referred expert and may request user authorization to accomplish this task.

In some embodiments, when a expert 204 or their associate cannot provide a scheduled or on-demand service for client/user 202 who is in their waiting room, the expert or associate may move the client 202 from their waiting room and place them in an alternate expert's waiting room. This process may or may not require user authorization. In some of these embodiments, the expert 204 may access a dashboard or utility app provided by the platform 203. This dashboard may comprise of a display with a list, icons or other indicia representing alternative experts and similar but distinct indicia representing clients 202 in the expert's waiting room. The transfer may be accomplished by dragging and dropping or other selection methods whereby the user 202 is transferred over to the waiting room of the alternative expert. This can also be done by selecting a provider through a list or other type of option pool.

Some embodiments of the present invention may comprise a single common entrypoint virtual waiting room.

Some embodiments of the present invention may comprise a platform 203 with a network of connected virtual waiting rooms associated with experts 204 who provide services through the platform 203. These waiting rooms provide a launch point for providing services to users 202 who have scheduled appointments for services and who have indicated their readiness to receive services by entering the virtual waiting room. Access to these users 202 may be controlled by waiting room management methods whereby one or more experts 204 may lend control of their waiting rooms to another expert or experts. The expert dashboard or another interface may be used by an expert to provide control of their waiting room to another expert and to accept control of other expert's waiting rooms. Using these methods, an expert may send one or more users in their own waiting room to another expert's waiting room. This may be performed when an expert's availability changes at the last minute.

In some embodiments, a first expert 204 may assume control of another expert's waiting room and users therein by an assignment process completed by an administrator or the other expert. The first expert may then access users in the other user's waiting room and perform services as if the user was in their own waiting room. The first expert may also redirect users in the other user's waiting room as if the users were in the first expert's waiting room.

In some embodiments, waiting room management methods may allow an expert to send users/clients 202 in their own waiting room to another waiting room associated with another expert. In some cases, an expert will have ultimate control of their waiting room such that control by other experts is only possible by express grant of permissions.

In some embodiments, an expert or administrator may control whether the waiting rooms they occupy can be manipulated by other experts and/or staff. A user 202 may specify that they will only deal with the experts with which they have expressly scheduled appointments.

In some embodiments, an expert 204 who is with a client 202 in a session 238, an expert 204 who is not in a session, a client 202 who is in a session or a client 202 outside a session may select another expert or be automatically or manually assigned another expert to join in a waiting room or active session or be included in an appointment.

In some embodiments, a client 202 can create a record using expert services 203 and share that record with an expert 204 before, after or during a session. A client record can be created without scheduling a session. For example, a client may create a video record of responses to questions listed on a document and send that record to an expert for evaluation before scheduling a session. Experts may also share information with a client or with another expert with whom they share an organization affiliation.

In some embodiments, an expert 204 or client 202, during a session, may invite one or more other experts 204 or clients 203 in the session to participate in a social media network with in-session links to social media functions. Using these features of the platform 203, a session participant may select other session participants, through a list, icon or other selection, to become friends, associates, sponsors or other social media connections. This could also be used in linking apps, i.e. an activity band monitor, smart watch, Google glass apps that are also collecting and/or sharing information.

In some embodiments, a client 202 using the platform 203 may connect with experts 204 via a session 238 or outside a session and share photos, test results or other information. If conditions allow, a client 202 may receive immediate answers, treatment and/or referrals in response to sharing this information.

In some embodiments, a client 202 may access, in an initial web page, waiting room or at another virtual location on the platform 203, a plethora of questions posed to clients 202 or other persons. These questions may be indexed by client type, by age, by client situation, by marital status, by gender, by physical ailment, by psychological condition or by other conditions. In some embodiments, a client 202 may also access questions posed by other clients 202 in relation to using the platform 203. For example, a system usage frequently-asked-questions (FAQ) database may be accessible from platform pages.

In some embodiments, the services platform 203 may comprise an automated or manual scheduler that can access the expert's calendar to determine if an appointment is imminent and identify a user scheduled for an appointment on the calendar. The scheduler may also search a list of logged-in users to find the scheduled user and admit that user into the expert's virtual waiting room when the expert 204 has indicated a readiness to receive the user 202.

In some embodiments of the present invention, a client/user 202 may select an expert 204 from a list, search results or some other selection format on an initial web page and share a text file, audio file, video file, document file or some other digital file with that expert.

In some embodiments, an expert 204 may request records electronically from a user/client 202 via web pages of the platform 203. When the user 202 is registered in the system, the expert may locate the user on a list or search results and send a request to that user 202 wherein the request is sent to the user's registered email or via an internal messaging system between registered users 202 and experts 204. When a user is not yet fully registered, but contact information is available in the system, the expert 204 may send an email, phone other message to the client 202 using the client's contact information.

In some embodiments of the present invention, an expert 202 or staff member may access a calendar system implemented by the services platform 203. Using the calendar system, the expert may indicate availability by partial hours, hours, days, weeks and/or months. The calendar can be customized for the times and session lengths desired by the expert 204. The calendar system may provide for booking appointments and may keep track of all appointments and free time periods. A calendar may show all appointments scheduled for online video sessions, online chat sessions, phone sessions and office appointments. The calendar would not show booked appointments that do not directly involve the client. The calendar may be available for booking appointments by the expert 204 and their staff and may further provide a user/client interface allowing clients 202 to access the calendar and book appointments.

In some embodiments, a calendar may be accessible by registered users as well as non-registered users who may access the calendar through a public facing portion of a website accessible to the public.

In some embodiments, a client 202 may access a chat interface in an initial web page, registered user page, expert's waiting room or other locations provided by the platform 203. This chat interface may connect any user 202 with any expert 204 for consultation within parameters set by the expert 204 or administrator. In some embodiments, a chat interface may comprise the messaging functions for leaving a message for a user 202 or expert 204 who is not currently available.

In some embodiments, an expert 204 or client 202 may lock or unlock a session to prevent or allow other parties to enter the session. A client 202 or expert 204 may ensure privacy during a session with this feature or they can also password protect a waiting room.

Some embodiments of the present invention provide for group sessions, wherein a plurality of clients 202 and/or experts 204 can participate in a single session. Typically a video or audio session is used. In these embodiments, multiple participants may be shown in individual windows on a participant's computer or mobile device screen. Video and audio for each participant may be controlled separately for each participant's window. Window size, orientation and screen location may be customized by a user 202 or an expert 204 for each session.

Figure 5:
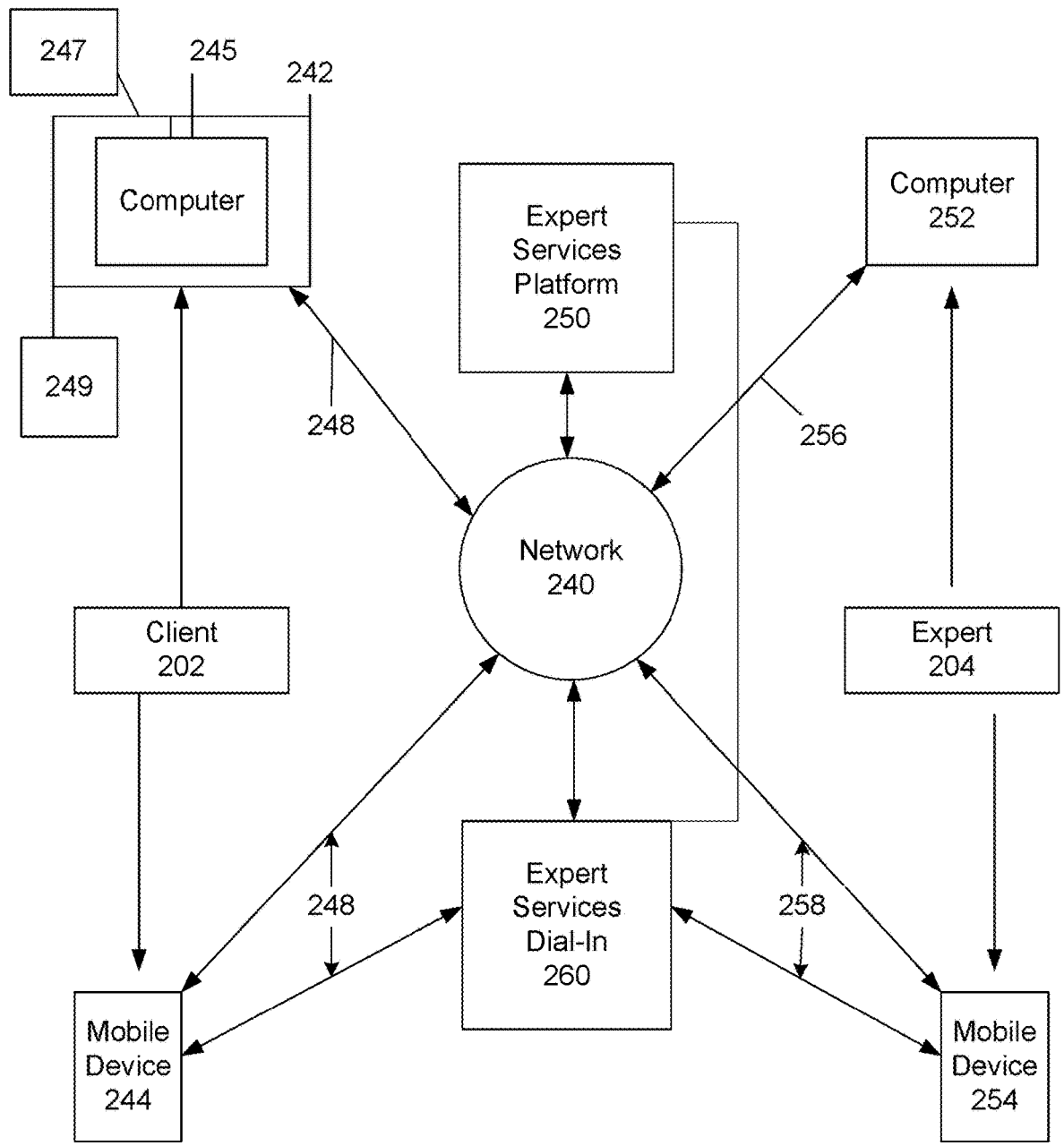
FIG. 5 shows an exemplary embodiment comprising client and expert devices and an expert services platform.

Some embodiments of the present invention may be described with reference to FIG. 5. FIG. 5 illustrates embodiments comprising an expert services platform 250 that is electronically and communicatively connected to a network 240 (e.g., the internet, business network, private or public LAN, etc.). In these embodiments, a client or user 202 may gain access to the expert services platform 250 by using a computing device 242 with a wireless or wired internet connection or network connection 246, such as an IEEE 802.11 a, b, e, g, n, Bluetooth or another connection. A client may also gain access to some expert services platform 250 functions from a mobile computing device 244, which may also connect via a wired or wireless network connection, but which may also connect using a wireless phone network connection 248 such as a cell phone service.

One or more experts 204 may also gain access to the expert services platform 250 from their computing devices 252 with network connections 256 or from their mobile computing devices 254 with wireless network and/or phone network connections 258 that connect via a network or internet 240.

Due to the various device types and connection types, some embodiments of expert services platform 250 may comprise functions for switching between connection types when a client 202 or expert 204 desires the mobility of a mobile device or the enhanced functionality of a PC-type computer, such as Google Glass, next generation communication tools like virtual reality, holograms or brain implants.

In some embodiments, a client computing device 242 may comprise an internal web camera 245. Some embodiments may also comprise an alternative web camera 247. Client mobile computing devices 244 may also comprise one or more cameras (not shown). Some embodiments of the present invention may also comprise biometric sensors or physiological sensors 249 which may measure physiological characteristics of a client/user 202. These physiological characteristics may be recorded locally on the client computing device 242, 244, may be transmitted to the expert services platform 250 for recording and storage or may be transmitted directly to an expert for analysis, recording and/or storage on an expert computing device 252 or to another software platform, a network, another software platform or records system or stored remotely.

In some embodiments of the present invention, an expert 204 may access their waiting room to connect with a client 202 for an expert session. If the client 202 does not have access to their computing device 242, but has access to a mobile device 244 with a phone network connection 248, the client may dial-in using a cell phone connection to an expert services dial-in service 260. The expert services dial-in service 260 may then convert the call to an internet protocol voice stream and forward the call through the expert services platform 250 to connect with an expert 204 through their expert computing device 252. Likewise, an expert 204 may also connect to a client 202 by telephone 254 by calling into expert services dial-in 260 and being routed to the expert services platform 250 or accessing the session by land line.

If a client 202 or expert 204 needs to switch between a telephone connection and an internet connection, the expert services platform 250 may provide for options for switching to or from a telephone call before or after a session or other communication has begun.

In some embodiments, an expert dashboard feature may allow an expert 204 to select a direct dial all feature that redirects the voice or video feed of a session or group session to the expert's phone or computing device. Accordingly, the direct dial all will allow an expert 204 to transfer all voice feeds in a session to the expert's phone through a phone network thereby allowing an expert 204 to take a session mobile if a need arises.

Some embodiments of the present invention may comprise functions for control of multiple cameras 245, 247 or other devices during a session or other communication. These functions may be located in a user session control page and/or an expert dashboard page or another location. These functions may allow a user to control all cameras and/or other devices during a session and to select which ones will be active during a session. These functions may also allow a user to relinquish control of any cameras to an expert so that an expert can remotely control the user's cameras during a session or another communication. Using these functions, an expert may be able to focus on and/or zoom into a user's facial features during a session to gain insight into the user's psychological or physical state during a session or other communication. Other devices which may be remotely controlled are biometric or biofeedback measuring devices, devices for administering medication or for taking readings remotely through a device such as a pulse oximeter.

The user access pages and/or expert dashboard pages of some embodiments may further comprise soft buttons or other selection methods allowing a user or expert to capture still images or readings. These still images may be captured during an on-going video session. The still images may be automatically sent through a secure internet e-mail system, by encrypted file transfer or by other methods. These still images or readings may be automatically displayed to an expert for inspection during a session as part of a web-based interface or by other methods. The still images may also be manually or automatically uploaded to a cloud-based records system maintained by the expert services platform 250.

Similarly to the cameras, a user computing device 242, 244 may comprise one or more audio capture devices (not shown). These audio capture devices may be controlled by the user or the user may relinquish control of those devices in the same manner as the cameras thereby enabling an expert to control the audio capture devices during a session or another communication.

In some embodiments, video and audio can be separately controlled by the user and/or the expert so that a session or communication may be set to audio-only, video-only, muted, video paused and other settings in a video or audio conference.

In some embodiments of the present invention, a video or audio conference session may be paused or muted to allow a participant, user 202 or expert 204, to record an audio dictation record. This audio recording may also be performed after a session. This recording may then be automatically appended to a session record and/or made available for use from the session page.

Some embodiments may comprise options in user 202's pages or a waiting room that allows a user to control the amount of personal information included in external notifications. In these embodiments a user may access an interface that allows the user 202 to select specific categories of information that will be transmitted to and accessible to each expert and that each expert, staff member and client.

In some embodiments, a user 202 may be provided with features, in a user page, a waiting room, a session page or another location, that allow the user to upload files using a secure intranet e-mail system implemented by expert services platform 250.

Some embodiments of the present invention may employ biometric sensors, psychological characteristic sensors or physiological characteristic sensors 249 to detect physiological or psychological characteristics or indicators of a user 202 during a session. This physiological or psychological data may be detected and recorded independently of other data or may be detected during and along with audio and/or video data in a session or displayed during the session. Some embodiments may function as a pass through for any data captured. The data may or may not be recorded. In an exemplary embodiment, an expert 204 may interview a client 202 in a video session while monitoring physiological or psychological data during the session. In another exemplary embodiment, a session may comprise monitoring physiological or psychological data while a user 202 is sleeping and no audio or video data is collected, but the data is uploaded in real time to an expert 204 for monitoring and analysis purposes. In this manner, an expert 204 may use a browser to access a web page of the expert services platform 250 that provides access to a client's biometric, biofeedback or other physiological or psychological data in real time or playback of recorded data.

Additionally, the physiological or psychological data monitoring may be recorded in sync with video such that the physiological or psychological data may be correlated with questioning or prompts posed by an expert 204 and recorded as part of the session. The data stream would be separately recorded and linked to the session record.

In some embodiments, one or more experts 204 may initiate communication with a client 202 and capture vital signs, diagnostic data, images and other data while conducting a real-time video conference consultation. In some cases, a store-and-forward technique may be used with secure data. In some cases, persistent vital sign data may be displayed throughout a session.

In some embodiments, a third party healthcare organization may receive and analyze collected data to improve healthcare delivery.

In some embodiments, synchronous video or audio consultation can be performed while simultaneously streaming high-resolution data such as EKG, general exam camera, ultrasound, otoscope, vital signs and other data in real-time.

In some embodiments, an expert 204 via the expert dashboard or another page, can share physiological or psychological data such as a vital sign record, lab report, images, referrals, prescriptions and discharge instructions with other authorized experts in the system or through external communication methods.

In some embodiments, after a consultation session, an expert 204 who is a doctor or medical specialist can write a prescription and send that prescription, via the expert services platform 250, to a participating expert pharmacist or to a non-participating pharmacist via external communication methods. That pharmacist may then send the prescription to the user 202. When all experts and the user are linked in their respective systems, the provider can write the prescription and then send it through an interface that places the order with the pharmacist's ordering system. The expert's service may be automatically billed to the user and the pharmacist charges may be automatically billed to the user with the proper authorizations. Accordingly, a paperless, efficient system is created for remote administration of some healthcare services.

In some embodiments of the present invention, an expert 204 can prepare treatment plans with the following features: diagnosis descriptions, diagnosis axis codes, GAF scores with descriptions, current risk assessments, concerns/issues, short-term and long-term goals, treatment objectives, treatment strategy, interventions and other features. These treatment plans may be communicated to users 202 and other experts 204 using system communication features or external communication media.

In some embodiments, an expert 204 may create client progress notes and maintained accurate and up-to-date progress notes with the following features: diagnosis descriptions, diagnosis axis codes, GAF scores with descriptions, current assessments, symptom descriptions, treatment plan status, notes, a plan of action with interventions and other features. These progress notes may be recorded and linked with a user 202 and may be made available through the expert dashboard during sessions with the user 202. Notes could also be sent to an external records system through API or other interface. The notes may also be available after the session.

In some embodiments, an expert 204 can collect psychosocial history data including presenting problems, current symptom checklists, emotional/psychiatric history, family history, medical history, substance use history, developmental history, socio-economic history and other data. In some embodiments, this data can be collected by making electronic forms available in the expert's virtual waiting room. Data can be collected pre, during or post session.

In some embodiments, an expert 204 can collect information about difficulties due to health or mental health conditions. These conditions may include diseases, illnesses, short-term and long-term health problems, injuries, mental or emotional problems, drug problems, alcohol problems and other issues.

In some embodiments of the present invention, a system administrator or virtual system manager may compile, record and analyze system statistics. These statistics may be recorded with specific data for each user, each expert or for groups of user and experts. Data may also be collected anonymously with no specific identity information. This data may be reported to users, experts or other parties with proper authorization. The data can be shared or accessible with users with the appropriate privileges in the system. Data can also be exported out by users with the appropriate permission levels.

Figure 6:
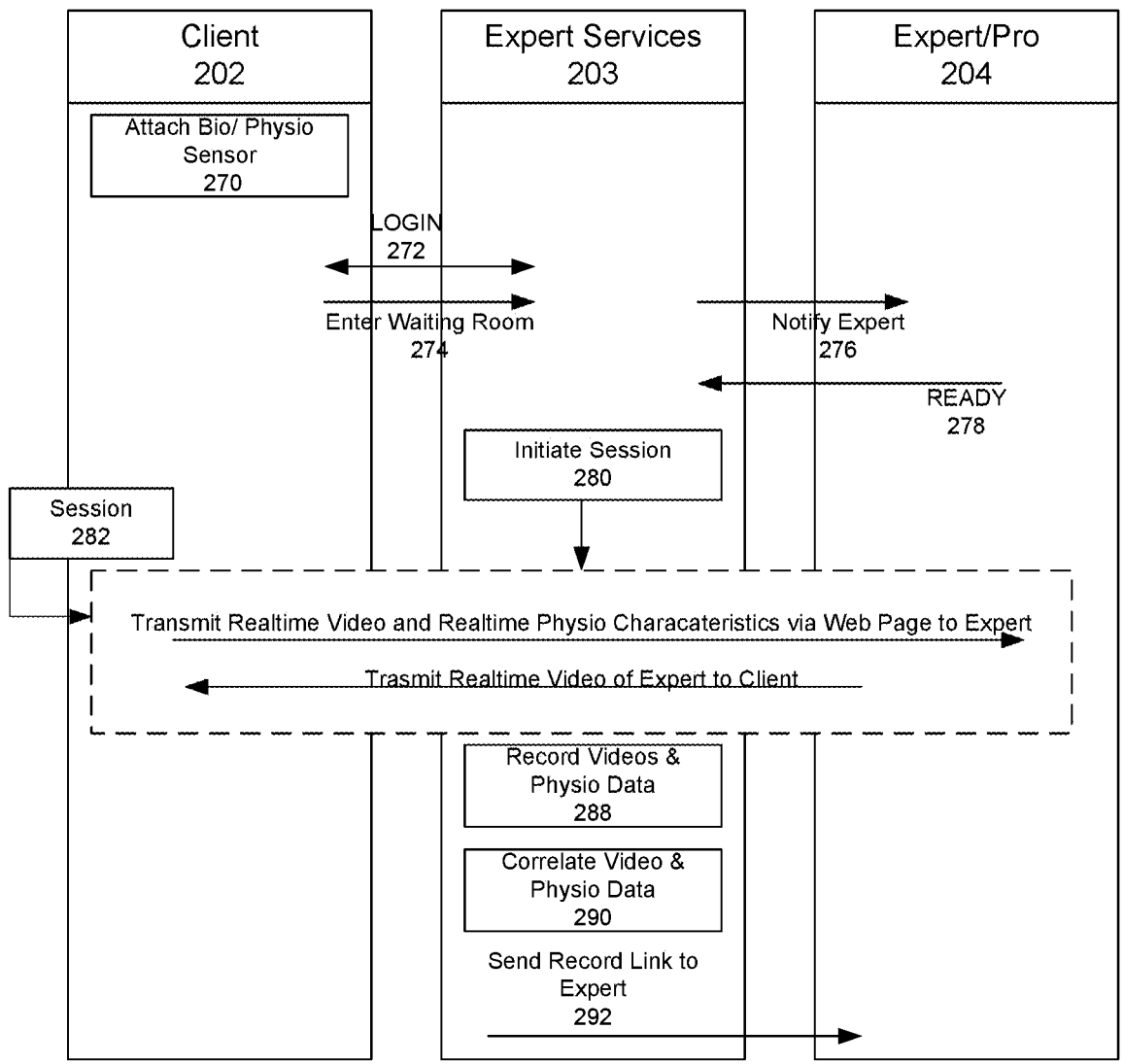
FIG. 6 shows an exemplary embodiments comprising transmission of physiological characteristic data during a session.

Some embodiments of the present invention may be described with reference to FIG. 6. In these embodiments an expert services platform 203 links clients 202 to experts 204.

These embodiments comprise biometric sensors or physiological or psychological characteristic sensors 249, which may be attached 270 to a client's body or in proximity to a client's body. These sensors may measure or detect heart rate, pulse profile, respiration rate, temperature, pupil dilation, stress level and other characteristics. Once the sensors are attached 270, the client 202 may log in 272 to the expert services website 203. To indicate a readiness to participate in a session with an expert 204, the client 202 may enter the expert's waiting room 274, by input in a web browser displaying expert services web page data.

Entry into the waiting room by the client 202 will trigger a notification 276 to the expert 204 that the client is ready for a session. In some embodiments, the notification 276 may comprise a notice regarding sensor data availability. In some embodiments, sensor data may be detected at this point and normal sensor output detection may be relayed to the expert 204. The expert 204, when ready, may respond to notification 276 by indicating a mutual readiness to commence by a readiness message 278 or by simply entering the waiting room as well.

When both parties have indicated readiness, the expert services platform may initiate 280 a session 282. In these embodiments, a session 282 may be accomplished by connecting the client 202 with the expert 204 over a network connection and may be facilitated by hosting an expert services web page with pages accessible by browser on the client's computer 242 and the expert's computer 252. In some embodiments, audio, video and physiological characteristic sensor outputs, or other sensor outputs, may be transmitted 284 from the client's computer or computing device 252 over an internet or network connection to the expert services server 203. At the expert services server 203, the audio, video and sensor outputs may be recorded 288, correlated 290, analyzed, converted and rerouted to associated web pages. In some embodiments, a correlated video and sensor output stream may be sent to an expert's computer 252 or other computing devices through a web page as part of the session 282. In some embodiments, the sensor outputs may be converted to a visual graphic display such as a graph, a multimedia display (e.g., heartbeat sound with graphics, pulse profile graph with oxygen saturation in color, etc.) These graphics may be sent to and displayed on the expert's web page in real time during the session 282.

During the session, simultaneously with the transmission from client 202 to expert 204, video, audio and other data may be transmitted 286 from the expert 204 to the client 202 via the expert services platform 203. In some embodiments, audio and video may be sent from a web cam aimed at the expert thereby enabling the expert 204 to pose questions and maintain a dialog with the client 202 while monitoring the client's physiological or psychological condition on the expert's display. In some embodiments, a recording of the session may be stored on the expert services server 203 and a link to that record may be sent 292 to the expert for analysis and/or review. This data record may also be made available to the client 202 and may be forwarded, at the request of the client 202, to other experts in the system or outside the system by external communication methods.

Figure 7:
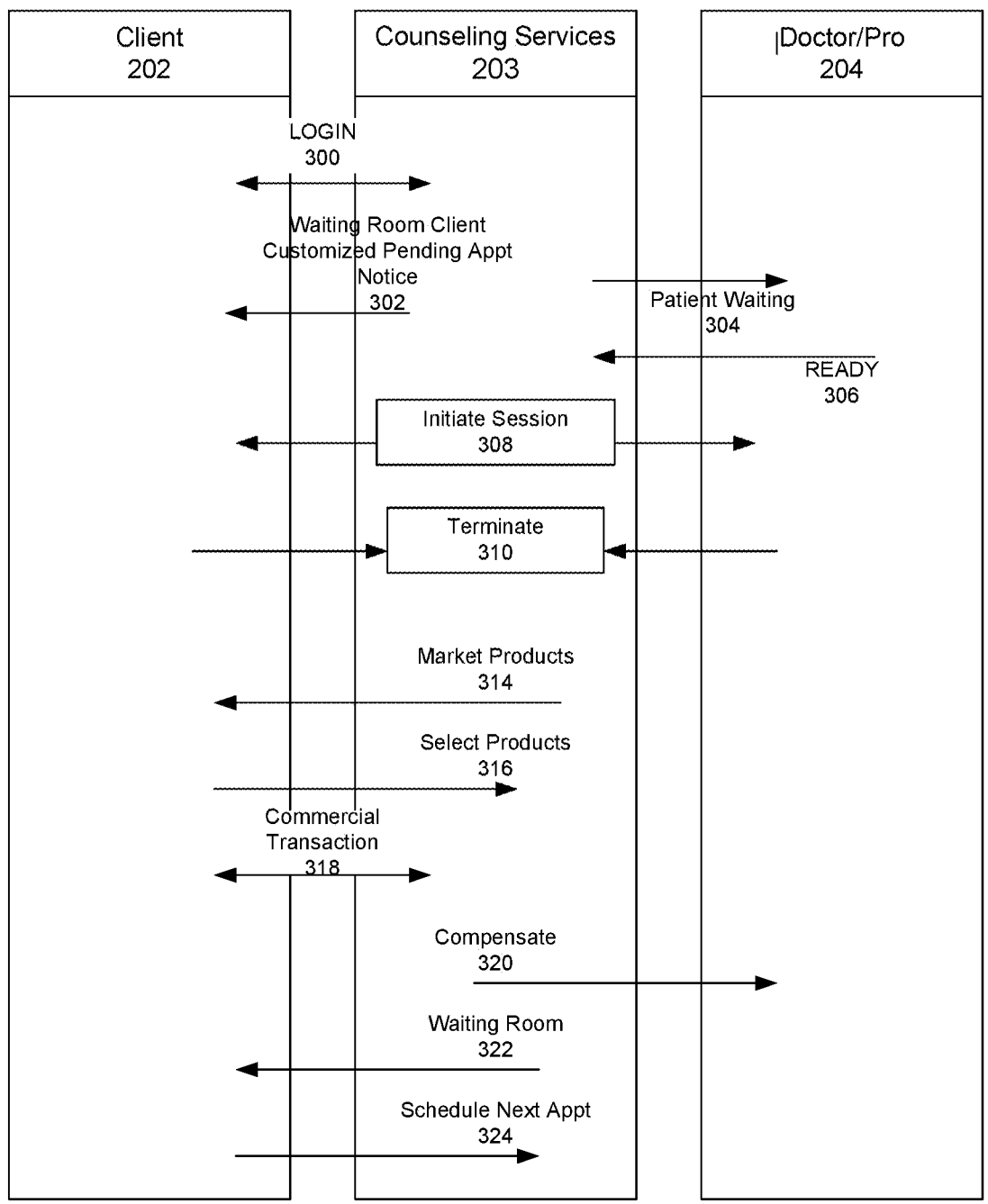
FIG. 7 shows an exemplary embodiment comprising marketing of products or services.

Some embodiments of the present invention may be described with reference to FIG. 7. In these embodiments an expert services platform 203 links clients 202 to experts 204. A client may log in 300 to gain access to expert services 203 web pages. After login, the services platform 203 may access the client's profile and use that data to customize a waiting room web page specifically for that client 202. An expert or expert's staff could customize a waiting room manually or it could be done automatically. Customization could include but is not limited to customized forms that must be completed before entering the session, or payment terms or customized media for the client to view. This customized waiting room may be served 302 to the client via the client's browser. If an appointment is imminent, the entry of the client 202 into the waiting room may signify a readiness to commence a session. Accordingly, the expert 204 may be notified 304 of the client's presence in the virtual waiting room.

When the expert 204 signals 306 a readiness to commence the session, the expert services platform 203 may initiate 308 a session. Typically a session may comprise simultaneous exchange of video and/or audio between client 202 and expert 204 in order to enable video chat and/or audio dialog and effect counseling and/or advice. During a session, an expert 204 may recommend one or more products, write prescriptions, recommend action plans, make reference to additional products or services that may benefit the client 202. When the participants 202, 204 finish the session, the session may be terminated 310.

After a session, or during a session, an expert 202 may indicate 312 that a client may benefit from or desire specific products or services that may be offered by vendors participating in the expert services platform 203. During a session or thereafter, the platform 203 may provide material 314 to the client. This provision may comprise material displayed to the client during the session or after the session. In some embodiments, web store pages may be displayed to the client 202 or links to web store pages may be sent to the client 202.

If a client desired to purchase a product or service offered to the client 202, the client 202 may select the product or service 316 and initiate an online commercial transaction 318 via expert services platform 203 web pages.

When a product or service is sold in response to an expert recommendation, prescription, endorsement or other message, the expert or organization may be compensated 320 with a percentage of the transaction or some other compensation scheme.

After a purchase or sales interaction, the client 202 may exit to the waiting room 322 and/or may schedule another appointment 324 before exiting the system.

While the foregoing advantages of the present invention are manifested in the detailed description and illustrated embodiments of the invention, a variety of changes can be made to the configuration, design and construction of the invention to achieve those advantages. Hence, reference herein to specific details of the structure and function of the present invention is by way of example only and not by way of limitation.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A method for remote consultation, said method comprising:
   configuring a sensor to sense physiological data of a patient, wherein said sensor is in sensing range of the patient and is communicatively connected through a network to an expert services platform hosted by a counseling server coupled to the network;

accessing, via a patient computing device coupled to the network, an initial web page provided by the counseling server by directing a web browser executing on the patient computing device to a universal resource locator (URL) associated with the initial web page;

transmitting a referral code entered by the patient via the patient computing device to the counseling server, wherein the referral code is issued by a first healthcare provider associated with the expert services platform and links the patient and a second healthcare provider associated with the expert services platform;

automatically directing the web browser of the patient computing device to a virtual waiting room web page associated with the second healthcare provider;

transmitting a notification to a provider computing device associated with the second provider and coupled to the network;

initiating a two-way audiovisual communication session between the patient computing device and the provider computing device;

transmitting audio communication between the patient and the second healthcare provider;

transmitting video of the patient from the patient computing device to the second healthcare provider;

transmitting physiological data from the sensor to provider computing device; and receiving, at the patient computing device, healthcare advice from the second healthcare provider, said advice being based on an analysis of said physiological data and said video communication, and said audio communication and other information gathered.

2. The method of claim 1 further comprising receiving video, audio or text from the second healthcare provider at the patient computing device during said consultation session.

3. The method of claim 1 wherein said physiological data comprises one or more of EKG data, general exam camera data, ultrasound data, otoscope data, vital signs data, fundus scope, dental exam scope, anterior lens scope, dermatology scope, and endoscope data, labs.

4. The method of claim 1 wherein said advice comprises a treatment plan comprising at least one of diagnosis descriptions, diagnosis axis codes, GAF scores with descriptions, current risk assessments, concerns/issues, short-term and long-term goals, treatment objectives, treatment strategy and intervention strategy, care plans and medication plans.

5. The method of claim 1 wherein said healthcare advice comprises a prescription.

6. The method of claim 1 wherein said healthcare advice comprises a notification that a prescription has been electronically sent to the patient's pharmacist.

7. The method of claim 1 wherein said physiological data is correlated with said video or audio data.

* * * * *